(12) United States Patent
McBeth et al.

(10) Patent No.: US 11,813,604 B2
(45) Date of Patent: Nov. 14, 2023

(54) PRINTED BIOGEL NANOSENSORS

(71) Applicants: Trustees of Boston University, Boston, MA (US); Fraunhofer USA, Inc., Plymouth, MI (US)

(72) Inventors: Christine McBeth, Everett, MA (US); Kirsten Borchers, Stuttgart (DE); Achim Weber, Altbach (DE); Daniel Zontar, Aachen (DE)

(73) Assignees: Trustees of Boston University, Boston, MA (US); Fraunhofer USA, Inc., Plymouth, MI (US); FRAUNHOFER-Gesellschaft zur Foerderung der angewandten Forschung e. V., Munich (DE)

( * ) Notice: Subject to any disclaimer, the term of this patent is extended or adjusted under 35 U.S.C. 154(b) by 0 days.

(21) Appl. No.: 17/740,014

(22) Filed: May 9, 2022

(65) Prior Publication Data
US 2022/0355302 A1    Nov. 10, 2022

Related U.S. Application Data

(60) Provisional application No. 63/186,385, filed on May 10, 2021.

(51) Int. Cl.
*B01L 3/00*     (2006.01)
*C12Q 1/6837*   (2018.01)
(Continued)

(52) U.S. Cl.
CPC .......... *B01L 3/5027* (2013.01); *C12Q 1/6837* (2013.01); *B01J 2219/00529* (2013.01);
(Continued)

(58) Field of Classification Search
CPC .. C12Q 1/6837; C12Q 1/6848; C12Q 1/6876; C12Q 2565/60; C12Q 2565/607;
(Continued)

(56) References Cited

U.S. PATENT DOCUMENTS

2005/0112634 A1*   5/2005   Woudenberg ....... B01L 3/50851
                                                          435/6.1
2014/0045701 A1*   2/2014   Esfandyarpour ....... B03C 5/026
                                                          506/26
(Continued)

FOREIGN PATENT DOCUMENTS

WO   WO-2020123309 A1 *   6/2020   ......... C12N 15/1065

OTHER PUBLICATIONS

Yu, Z.Q. et al., "Self-partitioning SlipChip for slip-induced droplet formation and human papillomavirus quantification with digital LAMP," Biosensors and Bioelectronics, vol. 155:112107, 7 pps., DOI:10.1016/j.bios.2020.112107 (2020).
(Continued)

*Primary Examiner* — Dennis White
(74) *Attorney, Agent, or Firm* — Burns & Levinson LLP; Steven M. Mills

(57) ABSTRACT

Disclosed is a biogel nanosensor for detection of an analyte that includes an acryloyl or methacryloyl modified hydrogel and nucleic acid amplification reagents in picoliter or nanoliter volume in the form of microarray. Also disclosed are methods of making the disclosed biogel nanosensor, and methods of using the biogel nanosensors.

20 Claims, 24 Drawing Sheets
Specification includes a Sequence Listing.

(51) Int. Cl.
    *B01L 7/00*     (2006.01)
    *C12Q 1/6848*     (2018.01)
    *C12Q 1/6876*     (2018.01)

(52) U.S. Cl.
    CPC .............. *B01J 2219/00576* (2013.01); *B01J 2219/00626* (2013.01); *B01L 7/52* (2013.01); *C12Q 1/6848* (2013.01); *C12Q 1/6876* (2013.01); *C12Q 2565/60* (2013.01); *C12Q 2565/607* (2013.01)

(58) Field of Classification Search
    CPC .... B01J 2219/00529; B01J 2219/00576; B01J 2219/00626; B01L 7/52
    See application file for complete search history.

(56) References Cited

U.S. PATENT DOCUMENTS

| | | | |
|---|---|---|---|
| 2014/0199276 A1 | 7/2014 | Xu et al. | |
| 2015/0293073 A1* | 10/2015 | Murphy | A61L 29/16 506/3 |
| 2018/0051310 A1* | 2/2018 | Hallock | C12Q 1/689 |

OTHER PUBLICATIONS

Yue, K. et al., "Synthesis, properties, and biomedical applications of gelatin methacryloyl (GelMA) hydrogels," Biomaterials, vol. 73, pp. 254-271, DOI: 10.1016/j.biomaterials.2015.08.045 (2015).
Yuk, H. et al., "Tough bonding of hydrogels to diverse non-porous surfaces," Nature Materials Let., vol. 15, pp. 190-198 (2015).
Chaouch, M., "Loop-mediated isothermal amplification (LAMP): An effective molecular point-of-care technique for the rapid diagnosis of coronavirus SARS-CoV-2," Rev. Med. Virol., vol. 31:e2215, 9 pps., DOI:10.1002/rmv.2215 (2021).
Deprez, L. et al., "Validation of a digital PCR method for quantification of DNA copy number concentrations by using a certified reference material," Biomol. Detect. Quantif., vol. 9, pp. 29-39, DOI:10.1016/j.bdq.2016.08.002 (2016).
DePuig, H. et al., "Minimally instrumented SHERLOCK (miSHERLOCK) for CRISPR-based point-of-care diagnosis of SARS-CoV-2 and emerging variants," Science Adv., vol. 7:eabh2944, 12 pps. (2021).
Joung, J. et al., "Point-of-care testing for COVID-19 using SHERLOCK diagnostics," medRxiv 2020.05.04.20091231; DOI:10.1101/2020.05.04.20091231 (2020).
Rabe, B. and Cepko, C., "SARS-CoV-2 detection using isothermal amplification and a rapid, inexpensive protocol for sample inactivation and purification," PNAS, vol. 117, No. 39, pp. 24450-24458, DOI:10.1073/pnas.2011221117/-/DCSupplemental (2020).
Wang, Y. et al., "Development of a Photo-Crosslinking, Biodegradable GelMA/PEGDA Hydrogel for Guided Bone Regeneration Materials," Materials, vol. 11, 1345, 12 pps., DOI:10.3390/ma11081345 (2018).
Yuan, Z. et al., "Injectable GelMA Cryogel Microspheres for Modularized Cell Delivery and Potential Vascularized Bone Regeneration," Small 2021, 17, 2006596, DOI:10.1002/smll.202006596 (2021).
Invitation to Pay Additional Fees in PCT/US22/28346 dated Jul. 29, 2022, 2 pps.
International Search Report and Written Opinion in Application No. PCT/US22/28346 dated Sep. 21, 2022 (17 pgs.).
Linnes, J. C. et al., "Polyethersulfone improves isothermal nucleic acid amplification compared to current paper-based diagnostics," Biomed Microdevices, vol. 18:30, 12 pps., DOI:10.1007/s10544-016-0057-z (2016).
Liu, J. et al. "Aptamer-incorporated hydrogels for visual detection, controlled drug release, and targeted cancer therapy," Anal Bioanal Chem, vol. 402, pp. 187-194, DOI:10.1007/s00216-011-5414-4 (2012).
Liu, Q. et al., "Bonding dissimilar polymer networks in various manufacturing processes," Nature Communications, vol. 9:846, DOI:10.1038/s41467-018-03269-x (2018).
Liu, R. et al., "Design and Synthesis of Target-Responsive Aptamer-Cross-linked Hydrogel for Visual Quantitative Detection of Ochratoxin A," ACS Applied Materials & Interfaces, vol. 7, pp. 6982-6990, DOI: 10.1021/acsami.5b01120 (2015).
Lopez-Jimena, B. et al., "Development and validation of four one-step real-time RT-LAMP assays for specific detection of each dengue virus serotype," PLoS Neglected Tropical Diseases, 12(5):e0006381, 22 pps., DOI:10.1371/journal.ontd.0006381 (2018).
Mamaghani, K. R. et al., "Synthesis and microstructural characterization of GelMa/PEGDA hybrid hydrogel containing graphene oxide for biomedical purposes," Materials Today Proceedings, vol. 5, pp. 15635-15644 (2018).
Mauk, M. G. et al., "Simple Approaches to Minimally-Instrumented, Microfluidic-Based Point-of-Care Nucleic Acid Amplification Tests," Biosensors, vol. 8, 17, 30 pps., DOI:10.3390/bios8010017 (2018).
Meagher, R. J. et al., "Impact of primer dimers and self-amplifying hairpins on reverse transcription loop-mediated sothermal amplification detection of viral RNA," Analyst, vol. 143, pp. 1924-1933, DOI:10.1039/c7an01897e (2018).
Messina, J.P. et al., "The current and future global distribution and population at risk of dengue," Nature Microbiol., vol. 4, pp. 1508-1515, DOI:10.1038/s41564-019-0476-8 (2019).
Mitra, R. D. & Church, G. M., "In situ localized amplification and contact replication of many individual DNA molecules," Nucleic Acids Research, vol. 27, No. 24, 6 pps. (1999).
Mujawar, L. H. et al., "Influence of the relative humidity on the morphology of inkjet printed spots of IgG on a non-porous substrate," RSC Advances, vol. 4, pp. 19380-19388, DOI:10.1039/c4ra01327a (2014).
Nakai, S., "Measurement of Protein Hydrophobicity," Current Protocols in Food Analytical Chemistry, B5.2.1-B5.2.13, 13 pps., DOI:10.1002/0471142913.fab0502s09 (2003).
Nawattanapaiboon, K. et al., "SPR-DNA array for detection of methicillin-resistant *Staphylococcus aureus* (MRSA) in combination with loop-mediated isothermal amplification," Biosensors and Bioelectronics, vol. 74, pp. 335-340, DOI:10.1016/j.bios.2015.06.038 (2015).
Noshadi, I. et al., "In vitro and in vivo analysis of visible light crosslinkable gelatin methacryloyl (GelMA) hydrogels," Biomaterials Science, 5(10), 14 pps., DOI:10.1039/c7bm00110j (2017).
Notomi, T. et al., "Loop-mediated isothermal amplification of DNA," Nucleic Acids Research, vol. 28, No. 12, 7 pps. (2000).
Ogihara, H. et al., "Simple Method for Preparing Superhydrophobic Paper: Spray-Deposited Hydrophobic Silica Nanoparticle Coatings Exhibit High Water-Repellency and Transparency," Langmuir, vol. 28, pp. 4605-4608, DOI:10.1021/la204492q (2012).
Pai, N. P. et al., "Point-of-care testing for infectious diseases: diversity, complexity, and barriers in low and middle-income countries," PLOS Med., vol. 9, iss. 9, e1001306, DOI:10.1371/journal.pmed.1001306 (2012).
Paul, R. et al., "Advances in point-of-care nucleic acid extraction technologies for rapid diagnosis of human and plant diseases," Biosensors and Bioelectronics, vol. 169: 11292, 20 pps., DOI:10.1016/j.bios.2020.112592 (2020).
Peci, A. et al., "Prevalence of Co-Infections with Respiratory Viruses in Individuals Investigated for SARS-CoV-2 in Ontario, Canada," Viruses, vol. 13:130, 13 pps., DOI:10.3390/v13010130 (2021).
Pepelanova, I. et al., "Gelatin-Methacryloyl (GelMA) Hydrogels with Defined Degree of Functionalization as a Versatile Toolkit for 3D Cell Culture and Extrusion Bioprinting," Bioengineering, vol. 5:55, 15 pps., DOI:10.3390/bioengineering5030055 (2018).
Priye, A. et al., "A smartphone-based diagnostic platform for rapid detection of Zika, chikungunya, and dengue viruses," Scientific Reports, vol. 7:44778, 11 pps., DOI:10.1038/srep44778 (2017).
Rabiller-Baudry, M. et al., "Characterisation of cleaned and fouled membrane by ATR-FTIR and EDX analysis coupled with SEM: application to UF of skimmed milk with a PES membrane," Desalination, vol. 146, pp. 123-128 (2002).

(56) References Cited

OTHER PUBLICATIONS

Rahimpour, A. and Madaeni, S., "Improvement of performance and surface properties of nano-porous polyethersulfone (PES) membrane using hydrophilic monomers as additives in the casting solution," Journal of Membrane Science, vol. 360, pp. 371-379, DOI:10.1016/j.memsci.2010.05.036 (2010).

Reboud, J. et al., "Paper-based microfluidics for DNA diagnostics of malaria in low resource underserved rural communities," PNAS, vol. 116, No. 11, pp. 4834-4842, DOI:10.5525/gla.researchdata.722 (2019).

Rehman, F. et al., "Immobilization of acrylamide-modified oligonucleotides by co-polymerization," Nucleic Acids Research, vol. 27, No. 2, pp. 649-655 (1999).

Rodriguez, N. et al., "Paper-Based RNA Extraction, in Situ Isothermal Amplification, and Lateral Flow Detection for Low-Cost, Rapid Diagnosis of Influenza A (H1N1) from Clinical Specimens," Analytical Chem., vol. 87, pp. 7872-7879, DOI:10.1021/acs.analchem. 5b01594 (2015).

Rubina, A. et al., "Hydrogel drop microchips with immobilized DNA: properties and methods for large-scale production," Analytical Biochemistry, vol. 325, pp. 92-106, DOI:10.1016/j.ab.2003.10.010 (2004).

Sakthivel, K. et al., "High Throughput Screening of Cell Mechanical Response Using a Stretchable 3D Cellular Microarray Platform," Small Journal, vol. 16:2000941, 18 pps., DOI:10.1002/smll.202000941 (2021).

Sanders, R. et al., "Evaluation of digital PCR for absolute DNA quantification," Analytical Chemistry, vol. 83, pp. 6474-6484, DOI:10.1021/ac103230c (2011).

Senkbeil, S. et al., "Roll-to-plate fabrication of microfluidic devices with rheology-modified thiol-ene resins," J. Micromech. Microeng., vol. 26:075014, 9 pps., DOI:10.1088/0960-1317/26/7/075014 (2016).

St. John, A., and Price, C. P., "Existing and Emerging Technologies for Point-of-Care Testing," Clin. Biochem. Rev., vol. 35(3), pp. 155-167 (2014).

Taczala, J. et al., "Chemical Modification of Cellulose Microfibres to Reinforce Poly(methylmethacrylate) used for Dental Application," Materials, vol. 13:3807, 13 pps., DOI:10.3390/ma13173807 (2020).

Tang, J. and Xiao, P., "Polymerizing immobilization of acrylamide-modified nucleic acids and its application," Biosensors and Bioelectronics, vol. 24, pp. 1817-1824, DOI:10.1016/j.bios.2008.09.018 (2009).

Tang, Z. et al., "Loop-Mediated Isothermal Amplification-Coupled Glass Nanopore Counting Toward Sensitive and Specific Nucleic Acid Testing" Nano Letters, vol. 19, pp. 7927-7934, DOI:10.1021/acs.nanolett.9b03040 (2019).

Tanner, N., "Visual detection of isothermal nucleic acid amplification using pH-sensitive dyes," Biotechniques, vol. 58, pp. 59-68, DOI:10.2144/000114253 (2018).

Teoh, B. T. et al., "Early detection of dengue virus by use of reverse transcription recombinase polymerase amplification," Journal of Clinical Microbiology, vol. 53, No. 3, pp. 830-837, DOI:10.1128/JCM.02648-14. (2015).

Thekisoe, O. M. M. et al., "Stability of Loop-Mediated Isothermal Amplification (LAMP) Reagents and its Amplification Efficiency on Crude Trypanosome DNA Templates," J. Vet. Med. Sci., vol. 71(4), pp. 471-475 (2009).

Tian, K. et al., "Adhesion between Hydrophobic Elastomer and Hydrogel through Hydrophilic Modification and Interfacial Segregation," Applied Materials & Interfaces, vol. 10, pp. 43252-43261, DOI:10.1021/acsami.8b16445 (2018).

Tillib, S. et al., "Integration of multiple PCR amplification and DNA mutation analyses by using oligo-nucleotide microchip," Anal. Biochem., vol. 292, pp. 155-160, DOI:10.1006/abio.2001.5082 (2001).

Topkaya, S. N., "Gelatin methacrylate (GelMA) mediated electrochemical DNA biosensor for DNA hybridization," Biosensors and Bioelectronics, vol. 64, pp. 456-461, DOI:10.1016/j.bios.2014.09.060 (2014).

Van den Bulcke, A. I. et al., "Structural and Rheological Properties of Methacrylamide Modified Gelatin Hydrogels," Biomacromolecules, vol. 1, pp. 31-38, DOI:10.1021/bm990017d (2000).

Vanoss, C. J. et al., "Macroscopic-scale surface properties of streptavidin and their influence on aspecific interactions between streptavidin and dissolved biopolymers," Colloids & Surfaces B: Biointerfaces, vol. 30, pp. 25-36, DOI:10.1016/S0927-7765(03)00025-0 (2013).

Vinayaka, A. et al., "Pathogen Concentration Combined Solid-Phase PCR on Supercritical Angle Fluorescence Microlens Array for Multiplexed Detection of Invasive Nontyphoidal Salmonella Serovars," Analytical Chemistry, vol. 92, pp. 2706-2713, DOI:10.1021/acs.analchem.9b04863 (2020).

Visseaux, B. et al., "Prevalence of respiratory viruses among adults, by season, age, respiratory tract region and type of medical unit in Paris, France, from 2011 to 2016," Plos One, vol. 12(7):e0180888, 15 pps., DOI:10.1371/journal.pone.0180888 (2017).

Wang, D., "Evaluation and improvement of LAMP assays for detection of *Escherichia coli* serogroups O26, O45, O103, O111, O121, O145, and O157," African Health Sciences, vol. 17, iss. 4, pp. 1011-1021, DOI:10.4314/ahs.v17i4.8 (2017).

Wavhal, D. S. and Fisher, E. R., "Hydrophilic modification of polyethersulfone membranes by low temperature plasma-induced graft polymerization," Journal of Membrane Science, vol. 209, pp. 255-269 (2002).

World Health Organization, "Dengue: guidelines for diagnosis, treatment, prevention and control," World Health Organization, Geneva, Switzerland, 160 pps. (2009).

Xue, Y-Y. et al., "Development of a Paper-based Microfluidic Analytical Device by a More Facile Hydrophobic Substrate Generation Strategy," Analytical Biochemistry, vol. 525, pp. 100-106, DOI:10.1016/j.ab.2017.03.001 (2017).

Yang, J. et al., "Hydrogel Adhesion: A Supramolecular Synergy of Chemistry, Topology, and Mechanics," Advanced Functional Materials, vol. 30:1901693, 27 pps., DOI:10.1002/adfm.201901693 (2020).

Yao, Y. et al., "Rapid Detection of Influenza Virus Subtypes Based on an Integrated Centrifugal Disc," ACS Sensors, vol. 5, pp. 1354-1362, DOI:10.1021/acssensors.9b02595 (2020).

Abe, K. et al., "Inkjet-Printed Microfluidic Multianalyte Chemical Sensing Paper," Analytical Chemistry, vol. 80, No. 18, pp. 6928-6934 (2018).

Adessi, C. et al., "Solid phase DNA amplification: characterisation of primer attachment and amplification mechanisms," Nucleic Acids Research, vol. 28, No. 20, e87 (2000).

Ahmed, N. et al., "Nano-engineering and micromolecular science of polysilsesquioxane materials and their emerging applications," J. Materials Chem. A, vol. 7, pp. 21577-21604, DOI:10.1039/c9ta04575a (2019).

Alizadeh-Pasdar, N. and Li-Chan, E. C. Y., "Comparison of Protein Surface Hydrophobicity Measured at Various pH Values Using Three Different Fluorescent Probes," J. Agric. Food Chem., vol. 48, pp. 328-334 (2000).

Amsden, B.,"Solute Diffusion within Hydrogels. Mechanisms and Models," Macromolecules, vol. 31, No. 23, pp. 8382-8395, DOI: 10.1021/ma980765f (1998).

Aston, R. et al., "Evaluation of the impact of freezing preparation techniques on the characterisation of alginate hydrogels by cryo-SEM," European Polymer Journal, vol. 82, pp. 1-15 (2016).

Ball, C. S. et al., "Quenching of Unincorporated Amplification Signal Reporters in Reverse-Transcription Loop-Mediated Isothermal Amplification Enabling Bright, Single-Step, Closed-Tube, and Multiplexed Detection of RNA Viruses," Analytical Chemistry, vol. 88(7), pp. 3562-3568 (2016).

Balu, B. et al., "Fabrication of 'Roll-off' and 'Sticky' Superhydrophobic Cellulose Surfaces via Plasma Processing," Langmuir, vol. 24, pp. 4785-4790 (2008).

Becker, H., "It's the economy . . . ," Lab Chip, vol. 9, pp. 2759-2762, DOI: 10.1039/b916505n (2009).

Beyer, A. et al., "Fast-Track, One-Step *E. coli* Detection: A Miniaturized Hydrogel Array Permits Specific Direct PCR and DNA Hybridization while Amplification," Macromolecular Bioscience, vol. 16, pp. 1325-1333, DOI: 10.1002/mabi.201600098 (2016).

(56) References Cited

OTHER PUBLICATIONS

Bhatt, S. et al., "The global distribution and burden of dengue," Nature, vol. 496(7446), pp. 504-507, DOI:10.1038/nature 12060 (2013).
Birger, R. et al., "Asymptomatic Shedding of Respiratory Virus among an Ambulatory Population across Seasons," mSphere, vol. 3, iss. 4, e00249-18, DOI:10.1128/mSphere.00249-18 (2018).
Boehm, A. et al., "Covalent Attachment of Enzymes to Paper Fibers for Paper-Based Analytical Devices," Frontiers in Chemistry, vol. 6, Article 214, 10 pages (2018).
Brecher, C. et al., "Comparison of roll-to-roll replication approaches for microfluidic and optical functions in lab-on-a-chip diagnostic devices,"Proc. SPIE 9320, Microfluidics, BioMEMS, and Medical Microsystems XIII, 932008; doi: 10.1117/12.2077592 (2015).
Cai, L. et al., "A simple paper-based sensor fabricated by selective wet etching of silanized filter paper using a paper mask," Biomicrofluidics, vol. 8(5), pp. 056504-056508 (2014).
Cai, S. et al., "Phosphorothioated Primers Lead to Loop-Mediated Isothermal Amplification at Low Temperatures," Analytical Chem., vol. 90, pp. 8290-8294 (2018).
Cha, C. et al., "Tailoring Hydrogel Adhesion to Polydimethylsiloxane Substrates Using Polysaccharide Glue," Angewandte Chemie Int. Ed., vol. 52,pp. 6949-6952 (2013).
Chansoria, P. et al., "Characterizing the Effects of Synergistic Thermal and Photo-Cross-Linking during Biofabrication on the Structural and Functional Properties of Gelatin Methacryloyl (GelMA) Hydrogels," ACS Biomater. Sci. Eng., vol. 7(11), pp. 5175-5188, DOI:10.1021/acsbiomaterials.1c00635 (2021).
Choi, W. et al., "Hydrogel micropost-based qPCR for multiplex detection of miRNAs associated with Alzheimer's Disease," Biosensors and Bioelectronics, vol. 101, pp. 235-244 (2018).
Dahl, A. et al., "Quantitative PCR based expression analysis on a nanoliter scale using polymer nano-well chips," Biomedical Microdevices, vol. 9(3), pp. 307-314, DOI:10.1007/s10544-006-9034-2 (2007).
Damin, F. et al., "DNA microarray-based solid-phase PCR on copoly (DMA-NAS-MAPS) silicon coated slides: An example of relevant clinical application," Biosensors and Bioelectronics, vol. 78, pp. 367-373, DOI:10.1016/j.bios.2015.11.091 (2016).
Dorh, N. et al., "BODIPY-Based Fluorescent Probes for Sensing Protein Surface-Hydrophobicity," Scientific Reports, vol. 5.18337, 10 pps., DOI:10.1038/srep18337 (2015).
Drain, P. K. et al., "Diagnostic point-of-care tests in resource limited settings," Lancet Infect Dis., vol. 14, pp. 239-249, DOI:10.1016/S1473-3099(13)70250-0 (2014).
Fatin-Rouge, N. et al., "Diffusion and Partitioning of Solutes in Agarose Hydrogels: The Relative Influence of Electrostatic and Specific Interactions," J. Phys. Biochem., vol. 107, pp. 12126-12137, DOI:10.1021/jp0303164 (2003).
Fu, E., "Enabling robust quantitative readout in an equipment-free model of device development," Analyst, vol. 139, 4750-4757, DOI:10.1039/c4an01003e (2014).
Fujita, S. et al., "Hyaluronic Acid hydrogel crosslinked wit complementary DNAs," Advances in Polymer Tech., vol. 2020, Article ID:1470819, 7 pps., DOI: 10.1155/2020/1470819 (2020).
Gaines, M. L. et al., "Reduced Volume PCR Amplification Reactions Using the AmpFISTR® Profiler Plus™ Kit," Journal of Forensic Sciences, vol. 47, No. 6, Paper ID:JFS2002057_476, 14 pps. (2002).
Getachew, B. A. et al., "Self-Healing Hydrogel Pore-Filled Water Filtration Membranes," Environ. Sci. Technol., vol. 51, pp. 905-913, DOI:10.1021/acs.est.6b04574 (2017).
Glavan, A. C. et al., "Omiphobic 'RF Paper' Produced by Silanization of Paper with Fluoroalkyltrichlorosilanes," Adv. Funct. Mater., vol. 24, pp. 60-70, DOI:10.1002/adfm.201300780 (2014).
Gurukumar, K. et al., "Development of real time PCR for detection and quantitation of Dengue Viruses," Virology Journal, vol. 6:10, 8 pps., DOI:10.1186/1743-422X-6-10 (2009).

Heiniger, E. K. et al., "Comparison of point-of-care-compatible lysis methods for bacteria and viruses," J. Microbiol. Methods, vol. 128, pp. 80-87, DOI:10.1016/j.mimet.2016.07.007 (2016).
Hettiaratchi, M. et al., "A rapid method for determining protein diffusion through hydrogels for regenerative medicine applications," APL Bioeng., vol. 2:0261 10, 15 pps., DOI:10.1063/1.4999925 (2018).
Hoch, E. et al., "Chemical tailoring of gelatin to adjust its chemical and physical properties for functional bioprinting," Journal of Materials Chemistry B, vol. 1(41), pp. 5675-5685, DOI:10.1039/c3tb20745e (2013).
Hoch, E. et al., "Stiff gelatin hydrogels can be photo-chemically synthesized from low viscous gelatin solutions using molecularly functionalized gelatin with a high degree of methacrylation," Journal of Materials Science: Materials in Medicine, vol. 23(11), pp. 2607-2617, DOI:10.1007/s10856-012-4731-2 (2012).
Hoffmann, J. et al., "Universal protocol for grafting PCR primers onto various lab-on-a-chip substrates for solid-phase PCR," RSC Adv., vol. 2, pp. 3885-3889, DOI:10.1039/c2ra01250b (2012).
Huang, H. et al., "A gel-based solid-phase amplification and its application for SNP typing and sequencing on-chip," Analyst, vol. 134, pp. 2434-2440, DOI:10.1039/b915121d (2009).
Huggett, J. F. et al., "Considerations for Digital PCR as an Accurate Molecular Diagnostics Tool," Clinical Chemistry, vol. 61, iss. 1, pp. 79-88, DOI:10.1373/clinchem.2014.221366 (2015).
Jenkins, G. et al., "Printed electronics integrated with paper-based microfluidics: new methodologies for next- generation health care," Microfluid Nanofluid, vol. 19, pp. 251-261, DOI:10.1007/s10404-014-1496-6 (2015).
Jung, S. et al., "Multiplexed on chip real-time PCR using hydrogel spot array for microRNA profiling of minimal tissue samples," Sensors and Actuators B: Chemical, vol. 262, pp. 118-124, DOI:10.1016/j.snb.2018.01.228 (2018).
Kim, J. et al., "Multiplex real-time PCR using temperature sensitive primer-supplying hydrogel particles and its application for malaria species identification," Plos One 13(1):e0190451, 12 pps., DOI:10.1371/journal.pone.0190451 (2018).
Ko, H. et al., "A simple layer-stacking technique to generate biomolecular and mechanical gradients in photocrosslinkable hydrogels," Biofabrication, vol. 11:025014, DOI:10.1088/1758-5090/ab08b5 (2019).
Kolluri, N. et al., "Towards lab on-a-chip diagnostics for malaria elimination," Lab Chip, vol. 18, pp. 75-94, DOI:10.1039/c7lc00758b (2017).
Kopecek, J. and Yang, J., "Hydrogels as smart biomaterials," Polymer Int., vol. 56, pp. 1078-1098, DOI:10.1002/pi.2253 (2007).
Kreutz, J. E. et al., "Self-digitization chip for quantitative detection of human papillomavirus gene using digital LAMP," Lab Chip, vol. 19(6), pp. 1035-1040, DOI:10.1039/c8lc01223g (2019).
Lan, H. et al., "The Role of Surface Properties on Protein Aggregation Behavior in Aqueous Solution of Different pH Values," AAPS PharmSciTech, vol. 21:122, 13 pps., DOI:10.1208/s12249-020-01663-7 (2020).
Land, K.J. et al., "Unmet Diagnostics Needs for the Developing World," 21 pps. (online Dec. 2018). In: Land, K. (eds) Paper-based Diagnostics. Springer, Cham., DOI:10.1007/978-3-319-96870-4 (2019).
Lau, W. J. et al., "A review on polyamide thin film nanocomposite (TFN) membranes: History, applications, challenges and approaches," Water Research, vol. 80, pp. 306-324, DOI:10.1016/j.watres.2015.04.037 (2015).
Li, H. et al., "A strategy for strong interface bonding by 3D bioprinting of oppositely charged κ-carrageenan and gelatin hydrogels," Carbohydrate Polymers, vol. 198, pp. 261-269, DOI:10.1016/j.carbpol.2018.06.081 (2018).
Li, X. et al., "Photolithographic 3D microarray electrode-based high-performance non-enzymatic H2O2 sensor," Colloids and Surfaces A: Physicochemical and Engineering Aspects, vol. 628:127249, DOI:10.1016/j.colsurfa.2021.127249 (2021).
Li, Y. et al., "Size-based separation of supercoiled plasmid DNA using ultrafiltration," Journal of Colloid and Interface Science, vol. 472, pp. 195-201, DOI:10.1016/j.jcis.2016.03.054 (2016).
Claassen et al., "Quantification of Substitution of Gelatin Methacryloyl: Best Practice and Current Pitfalls," BioMacromolecules, Dec. 2017, pp. 1-41.

(56) References Cited

OTHER PUBLICATIONS

Liu et al., "Natural Polymers for Organ 3D Bioprinting," Polymers, vol. 10, No. 1278, Nov. 2018, pp. 1-26.

* cited by examiner

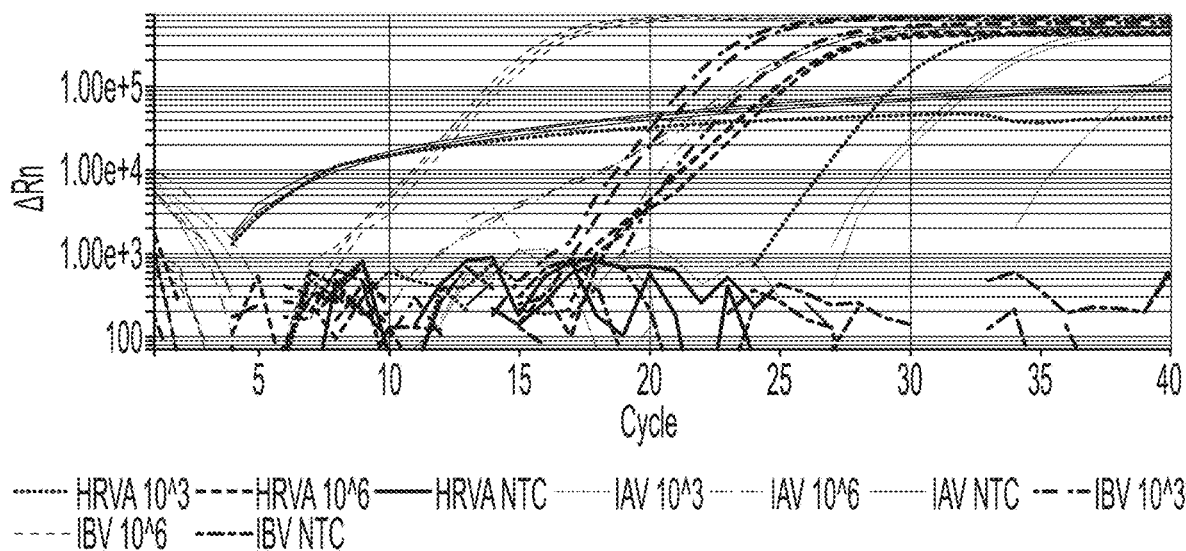
FIG. 7E
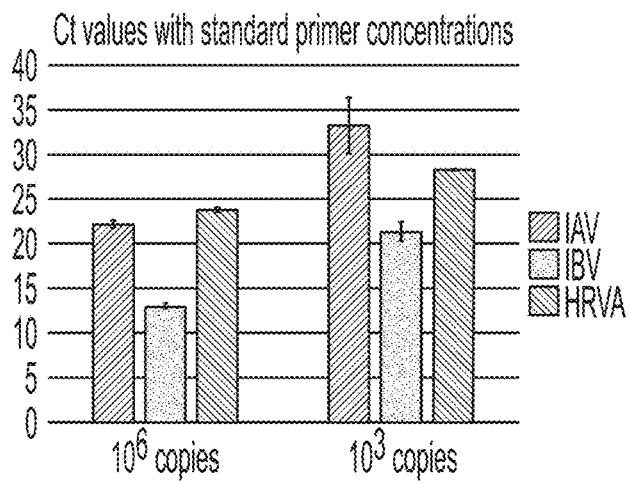
FIG. 7F
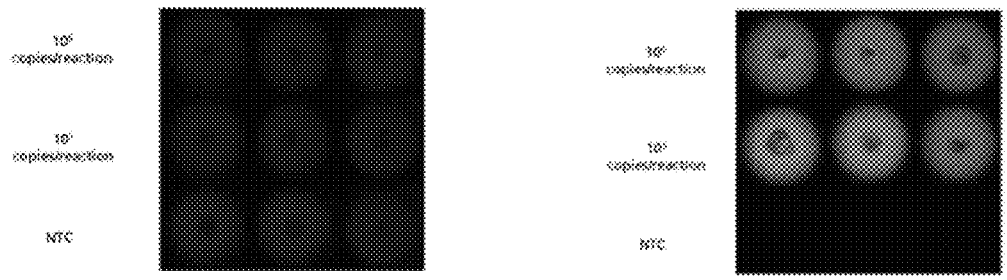
FIG. 7G
FIG. 7H 100 uM Fluorescein in 10% wt $GM_2A_8$ FIG. 10F
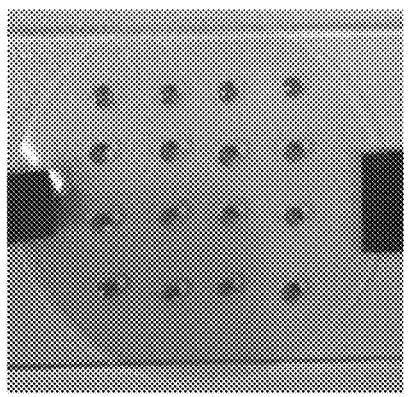
FIG. 10G
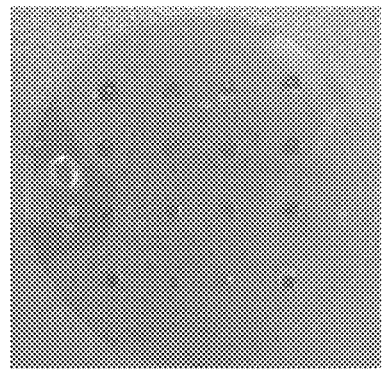
FIG. 10H

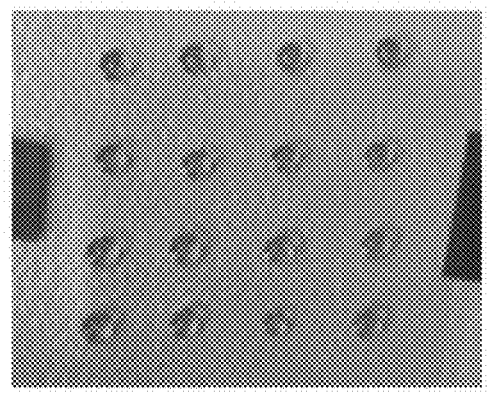
FIG. 10I
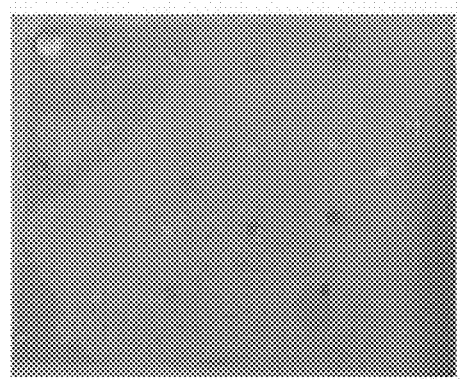
FIG. 10J
| Substrate / Time | 0.25 % TMOS | 1.0 % TMOS | 4.0 % TMOS | 8.0 % TMOS | 12.0 % TMOS |
|---|---|---|---|---|---|
| After crosslinking | | | | | |
| 5 min in water | | | | | |
| 24 hours in water | | | | | |
| After 48 h in water washing with wash bottle | | | | | |
FIG. 10K FIG. 10L
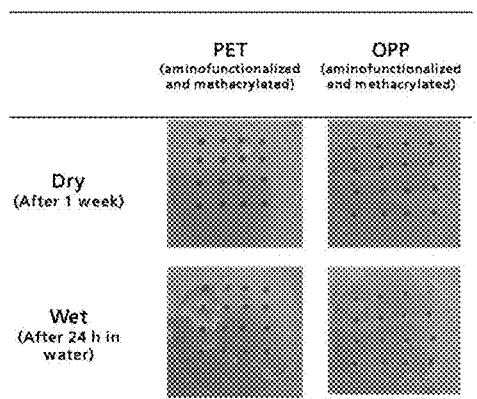
FIG. 10M
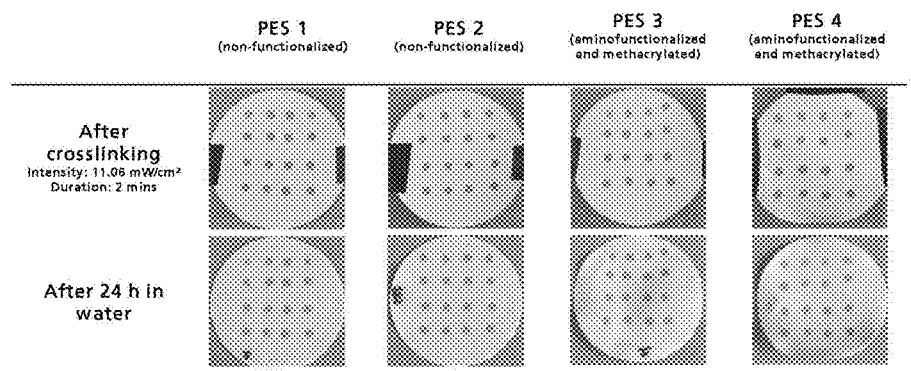
FIG. 10N

```
                        SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1
tggggtagca gactagtgg                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 2
tctgtgcctg gaatgatgc                                                    19

<210> SEQ ID NO 3
<211> LENGTH: 39
<212> TYPE: DNA
<213> ORGANISM: Artificial Sequence
<220> FEATURE:
<223> OTHER INFORMATION: Synthetic sequence

<400> SEQUENCE: 3
ccaccagggt acagcttccc gacccctccc aaaacacaa                              39

<210> SEQ ID NO 4
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 4
cyagaggtta gaggagaccc ccccaggatc tctggtctct ccc                         43
```

```
<210> SEQ ID NO 5
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 5
tggtgttggg ccccgct                                                    17

<210> SEQ ID NO 6
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 6
aaacagcata ttgacgct                                                   18
```

PRINTED BIOGEL NANOSENSORS

CROSS-REFERENCE TO RELATED APPLICATION

This application claims benefit under 35 U.S.C. § 119(e) of U.S. Provisional Application No. 63/186,385, filed May 10, 2021, the contents of which are incorporated herein by reference in their entirety.

SEQUENCE LISTING

The instant application contains a Sequence Listing that has been submitted electronically in ASCII format and is incorporated by reference in its entirety. Said ASCII copy, created on May 9, 2022, is named BOS-0020US_SL_ST25.txt and is 2,000 bytes in size.

TECHNICAL FIELD

The disclosed technology relates to biogel nanosensors, methods of making a biogel nanosensor, and methods of using a biogel nanosensor.

BACKGROUND

Both developed and developing countries face immense challenges in accurately diagnosing and responding to diseases (St John, et al. 2014). Limited access to centralized labs and highly trained staff in developing regions, in addition to recent severe infectious outbreaks of diseases like Covid-19, Ebola, Zika, dengue (Pai, et al. 2012), highlight the need for a diagnostic platform that can provide quick, simple screening and can be readily manufactured on a large scale for distribution. Emerging lab-on-a-chip technologies like microfluidic and paper-fluidic approaches (Kolluri, et al. 2017) show promise for developing diagnostics that satisfy the ASSURED (affordable, sensitive, specific, user-friendly, rapid and robust, equipment free, deliverable to end users) criteria published by WHO (Drain, et al. 2014). However, there is a significant gap between the development and implementation of these point-of-care devices (POC) in developing regions. A major barrier for the commercialization of POC diagnostic devices is their incompatibility with established large-scale manufacturing techniques (Brecher, et al. 2015; Senkbeil, et al. 2016; Becker, H. 2009). Processing costs can increase rapidly if device materials cannot facilitate commonly used techniques like printing, injection molding or a roll-to-roll production line. In order to enable large scale implementation of POC devices we need to work within the constraints present in low resource settings such as lack of funding, advanced infrastructure for manufacturing and skilled labor (Land, et al. 2019).

Dengue is the one of the most prevalent viral disease in humans, with 3.6 billion people living in areas with a significant risk of disease transmission and an estimated 96 million dengue cases annually (Bhatt, et al. 2013). Dengue virus (DENV) outbreaks in between 2006 and 2013, in countries like India, China, Singapore, Malaysia and Portugal (Lopez-Jimena, et al. 2018), highlight the necessity of rapid virus detection to identify DENV as the cause, in order to manage and control virus spread. However, the diagnosis of dengue virus infections cannot rely solely on clinical manifestations when many patients are asymptomatic. Therefore, rapid, accurate, relatively low-cost diagnostic tools for DENV are critical for effective disease management and control via mass screenings, especially in developing countries with limited and inaccessible health care resources. As recommended by the WHO Special Programme for Research and Training in Tropical Diseases (TDR) (WHO, 2009), the specifications of an ideal dengue test are that it should (i) distinguish between dengue and other diseases with similar clinical presentations (such as malaria, chikungunya, and other flaviviruses), (ii) be highly sensitive, (iii) provide rapid results, (iv) be inexpensive, (v) be easy to use, and (vi) be stable at temperatures above 30° C. for usage in the field and in primary health care settings, usually with very limited/no optimal storage options. Nucleic acid amplification tests (NAATs) are one such category of tests that have the potential to satisfy these conditions, and many others like them.

Isothermal NAAT methods, such as loop-mediated isothermal amplification (LAMP), have been used for rapid disease diagnosis in low resource settings due to their increased sensitivity and lack of thermal cycling. LAMP based NAATs are very popular tools for rapid point-of-care diagnostics because of their simplicity, rapid nature, specificity, sensitivity (Notomi, et al. 2000) and cost-effectiveness, as no special equipment is needed. LAMP can amplify up to $10^9$ copies of DNA in less than one hour under isothermal conditions (65° C.). Reactions can be visualized by monitoring either the turbidity or the fluorescence by visual inspection under UV lamp when using an intercalating dye or by color change. Fluorescent based LAMP readout techniques like QUASR also lend themselves to easy deployment in field settings via small reader devices such as smartphones. The conditions and equipment required for these techniques, however, remain complicated and costly, and not compatible with real-world point-of-care testing.

There is a need for a widely available diagnostic platform for diagnosis of diseases such as viral infections. Such a platform that can be easily manufactured on a large scale would be beneficial both for making clinical decisions as well as provide new tools to epidemiologists broadly screening the population during epidemic threats. A POC diagnostic device can realize the ASSURED criteria as well as be accessible in resource limited settings.

SUMMARY

This disclosure presents a biogel nanosensor for detecting an analyte in a sample including a modified hydrogel and nucleic acid amplification reagents at nanoliter volume on the surface of a substrate in a microarray form of spots, methods of making the biogel nanosensor, and methods of using the biogel nanosensor.

One aspect of the disclosed technology is a biogel nanosensor for detecting an analyte in a sample comprising an acryloyl or a methacryloyl modified hydrogel on the surface of a substrate, and nucleic acid amplification reagents, in which the hydrogel is crosslinked in picoliter or nanoliter volume on the surface of the substrate in a microarray form of spots, and the nucleic acid amplification reagents are added in picoliter or nanoliter volume to the hydrogel spots after crosslinking.

In embodiments, the biogel nanosensor further comprises a light guide that is included with the hydrogel and the nucleic acid amplification reagents. In embodiments, the biogel nanosensor includes a heating element. In some embodiments, the biogel nanosensor further includes a wicking matrix that may be applied over the biogel nanosensor microarray to deliver a sample to the biogel nanosensor microarray.

In embodiments, the hydrogel and nucleic acid amplification reagents are on the substrate in small volume of picoliters to nanoliters. In embodiments, the total volume of hydrogel and amplification reagents for each spot on the microarray is in the range of about 0.1 nL to about 10 nL. In some embodiments, the hydrogel and amplification reagents are each applied to the substrate in picoliter drops for each spot of the microarray.

Another aspect of the disclosure is a method of preparing a biogel nanosensor comprising obtaining an acryloyl or a methacryloyl modified hydrogel, applying the hydrogel in picoliter or nanoliter volume on the surface of a substrate in a microarray form of spots, crosslinking the hydrogel on the substrate surface, and combining, adding or applying nucleic acid amplification reagents in picoliter or nanoliter volume to the crosslinked hydrogel. In some embodiments, the method further comprises adding a light guide to the biogel nanosensor with the crosslinked hydrogel and amplification reagent microarray.

A further aspect of the disclosure is a method of detecting an analyte in a sample, comprising contacting a biogel nanosensor described herein with the sample; and measuring the presence of a detectable signal produced by the analyte in the sample. In some embodiments, measuring the presence of a detectable signal comprises applying a heating element to the biogel nanosensor after contact with the sample. In embodiments, applying a heating element to the biogel nanosensor initiates nucleic acid amplification with the nucleic acid amplification reagents and the sample, which may generate a detectable signal.

In a further embodiment, the method of detecting an analyte in a sample comprises connecting the biogel nanosensor to an analyzer or reading device for detecting and quantifying the analyte.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The teachings in the present disclosure will be more fully understood from the following description of various illustrative embodiments, when read together with the accompanying drawings. It should be understood that the drawings described below are for illustration purposes only and are not intended to limit the scope of the present teachings in any way.

FIG. 3A, the SD chip consists of an array of channels and wells that spontaneously compartmentalizes aqueous samples into defined volumes for digital nucleic acid quantification assays. FIG. 3B is a fluorescent image taken after the digital LAMP assay. The arrays consisted of 1536 wells with a well volume of 6.5 nL. Positive wells in which amplification occurred are more brightly fluorescent than negative wells.

FIG. 6A top row shows the endpoint fluorescent readout in Cy5 channel after amplification cycles of serially diluted RNA has ended (50 min). The limit of detection observed from fluorescent readout is $10^3$ copies per reaction. The results from all trials (n=9) were also fitted to a probit curve with shaded region indicating 95% confidence interval. FIG. 6B is a gel electrophoresis of optimized DENV RT-LAMP product.

FIGS. 7A-7M show end point readout of Cy5 fluorescent values for RT-LAMP with various viruses. FIG. 7A is a graphic of end point readout of Cy5 fluorescent values of DENV RT-LAMP assay at 25° C., serially diluted RNA amplified via RT-LAMP for 50 minutes and then brought down to an ambient temperature of 25° C. (n=3); fluorescent intensity recorded by QuantStudio5 via Cy5 channel at endpoint and mean values at each concentration were plotted. Error bars depict standard deviation values. Fluorescence was observed after amplification at the printed locations for two concentrations ($10^6$ copies and $10^3$ copies) each for Influenza A (FIG. 7B), Influenza B (FIG. 7C), and Rhinovirus (FIG. 7D). Amplification plot (FIG. 7E) and Ct value (FIG. 7F) show amplification detected for both RNA concentrations for all three viruses. Standard primer concentration, 1.6 µM FIP/BIP-Cy5, 0.2 µM F3/B3, 0.8 µM LF/LB (0.4 µM LF1 LF2 and 0.8 µM LB for Rhinovirus), 2.4 µM Quencher, 0.32 Units/µL Bst 2.0 WarmStart® Polymerase enzyme at 67° C. for 40 minutes. End point images were taken at 635 nm excitation at room temp. Fluorescence was not observed for two concentrations of SARS CoV-2 Orf1 (FIG. 7G), as compared to SARS CoV-2 N (FIG. 7H). LAMP assay for each virus with lower concentrations of sample for clinically reported lowest loads, at $10^1$ copies, $10^2$ copies, and $10^3$ copies each at an increased FIP/BIP-Cy5 to 4.8 µM, quencher 7.2 µM, and Bst 2.0 WarmStart® Polymerase enzyme to 0.64 Units/µL, and all 0.8 µM LF/LB. Influenza A not detected (FIG. 7I), Influenza B positive for all concentrations (FIG. 7J), and Rhinovirus (FIG. 7K) and SARS CoV-2 N (FIG. 7L) positive for $10^2$ and $10^3$ copies. FIG. 7M is a chart of acrydite primers and unmodified primers in DENV LAMP for varying concentration of RNA. N=3 except $10^3$ copies/uL data for master mix in gel with ACR primer sets n=2.

FIGS. 8A-8B illustrate degree of hydrogel swelling, and drying of hydrogels prior to assay decreases swelling. FIGS. 8C-8F illustrate drop formation of methacryloyl hydrogel. FIG. 8C illustrates 10% (w/v) $GM_{10}$ snapshot of drop (top left) indicates regular drop formation at the center of the nozzle and without any satellite drops, an array (top right) of 10% (w/v) $GM_{10}$ mixed with SYBR green labelled DENV plasmid DNAs spots printed on TMSMPA treated cyclo-olefin polymer (COP) strip, 50 drops per spot of 10% (w/v) $GM_{10}$ after printing (bottom left), and after drying in humidified chamber for 30 min (bottom right). FIG. 8D shows a snapshot of regular $GM_2A_8$ drop formation at 5% (w/v) in 5% glycerol (v/v), with labeled spots before (left) and after drying (right); FIG. 8E shows 10% (w/v) $GM_2A_8$ in 5% glycerol (v/v) snapshot of regular drop formation; probes used at room temperature, 500 pL volume per drop, 100 drops/spot. FIG. 8F is a snapshot of 10% (w/v) $GM_2A_8$ in glycerol mixed with LAMP regents with regular drop formation; 500 pL volume per drop, 80 drops/spot (40 nL total). DENV hydrogel-LAMP assay tests with printing on glass substrate, image results of lower volume 25 nL hydrogel and crosslinked, then 100 nL LAMP mix printed with sample, $2 \times 10^4$ copies per reaction, layered on the hydrogel spots (FIG. 8G), with image results of the assay with 100 nL hydrogel and then 100 nL LAMP mixed with sample layered on hydrogel spots (FIG. 8H), and image results of 100 nL hydrogel printed and crosslinked, LAMP reagent master mix at about 80 nL was printed on top of the hydrogel spots, and a sample at about 20 nL was printed on top of the hydrogel-LAMP spots. (FIG. 8I); UV crosslinking for 3 min at 8-9 mW/cm², 67° C. for 15 min, images at 635 nm.

FIGS. 9A-9B present fluorescently labelled BSA and DENV DNA target within 10% $GM_{10}$ at 65° C. to model diffusion of LAMP reagents within the hydrogel matrix. FIG. 9A, 5 µL spots of 10% $GM_{10}$ mixed with AF488-BSA were crosslinked and attached to a TMPSMA treated glass slide with SYBR green treated DENV DNA was added on top of 10% $GM_{10}$ spots. Fluorescent images were taken before adding JAB in the reservoir (marked as "before") and after every 15 minutes. FIG. 9B is a plot of the corresponding fluorescent intensity profiles across the spots at each timepoint. The type of hydrogel may have an effect on a small molecule fluorescein (about 332 Da) diffusion. Fluorescent intensity profiles across 10% $GM_2A_8$ (FIG. 9C), 10% $GM_{10}$ (FIG. 9D), 10% $GM_{90}$ (FIG. 9E), and 10% $GM_{160}$ (FIG. 9F). Fluorescence recovery after photobleaching (FRAP) diffusion with fluorescein in PBS (FIG. 9G), and fluorescein in gelatin with 10% $GM_2A_8$ hydrogel (FIG. 9H), were much slower than diffusion with FITC BSA in PBS (FIG. 9I), and FITC BSA in gelatin (FIG. 9J) using 10% $GM_2A_8$ hydrogel (100 ul of 10% $GM_2A_8$ in 5% glycerol). Capillary tube diffusion is another estimation model for diffusion parameters (FIGS. 9K-9L).

(FIG. 10O).

FIG. 14A is a photograph of the assembled device with inlet closed with PCR sealing tape. FIG. 14B illustrates an exploded view of the device three layers, the bottom acrylic layer with wells for holding the hydrogel based LAMP reaction, sample delivery channel made with double sided adhesive tape, and an acrylic cover with a sample delivery port to seal the device. FIG. 14C shows a Cy5 fluorescent ring around the crosslinked hydrogel indicating positive detection of target amplicon.

DETAILED DESCRIPTION

Definitions

Figure 1:
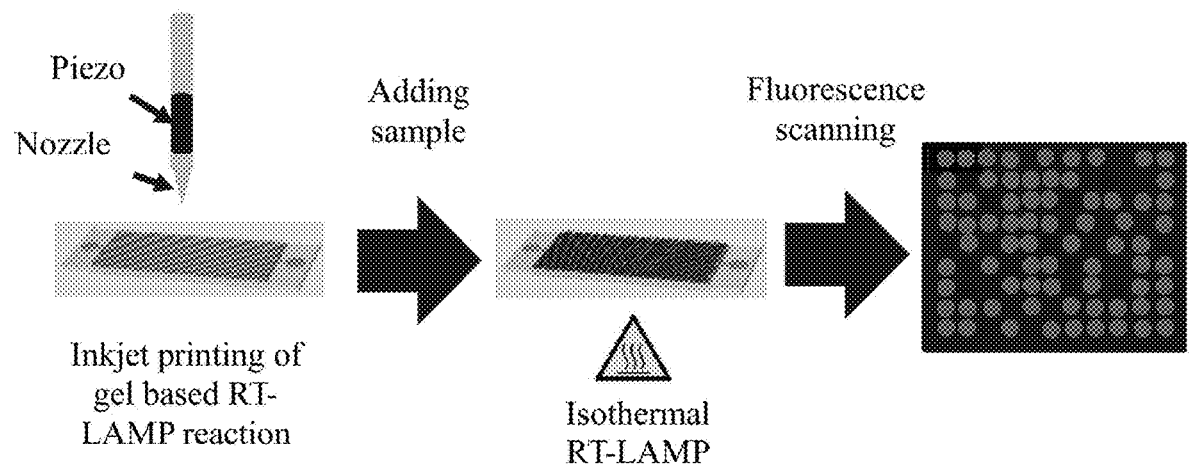
FIG. 1 depicts a diagnostic platform model. Following printing (piezo dispensary capillary shown in yellow) of reverse transcription (RT)-LAMP regents on top of a crosslinked hydrogel ($GM_{10}$) matrix on the substrate, the hydrogel spots will be interacted with sample. After isothermal heating, average fluorescent intensity of each well may be plotted and a threshold set to make a distinction between positive (target amplification) and negative wells.
Figure 2:
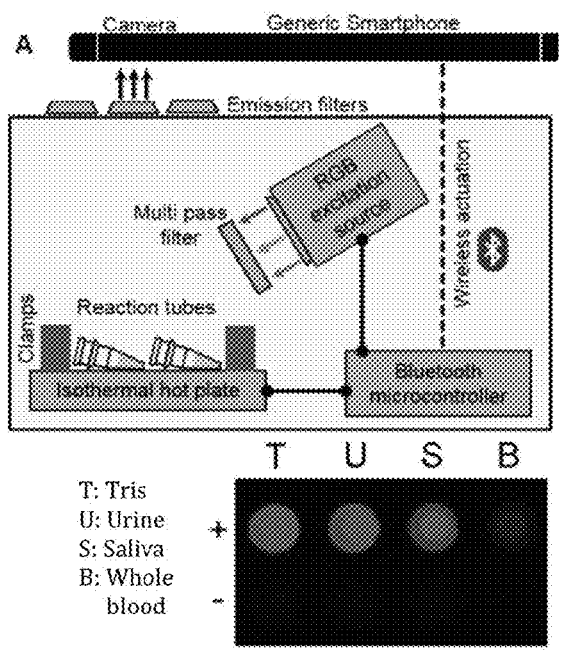
FIG. 2 illustrates smartphone based QUASR detection in complex sample matrices from Priye, et al., 2017. Schematic of RT-LAMP detection setup depicting the isothermal heater with reaction tubes, LED excitation source and Bluetooth microcontroller (Arduino Uno). QUASR detection in RT-LAMP preserves sensitivity in crude matrices. Image depicts positive and negative Zika virus (ZIKV) detection in matrices.
Figure 3A:
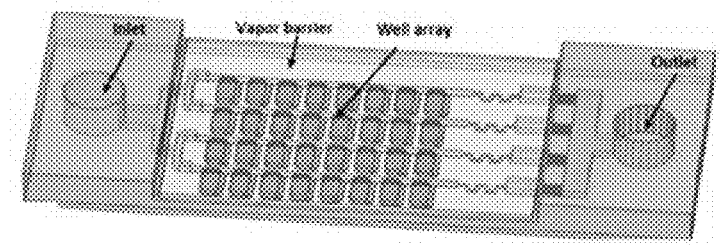
FIGS. 3A-3B represent a prior art self-digitization (SD) chip designed by Kreutz, et al., 2019.
Figure 3B:
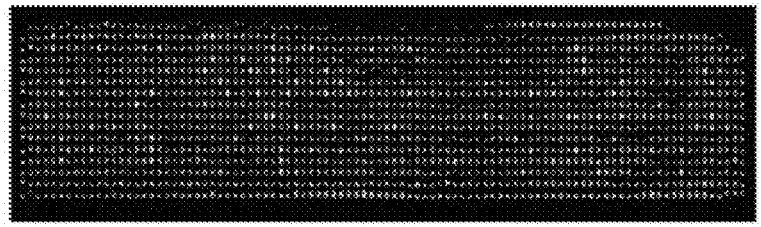

The terms "a," "an," "the" and similar references used in the context of the present disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The technology described herein relates to a biogel nanosensor for detecting an analyte in a sample comprising a methacryloyl hydrogel or a methacryloyl acetylated hydrogel on the surface of a substrate, and nucleic acid amplification reagents, in which the hydrogel is crosslinked in nanoliter volume on the substrate surface printed in a microarray, methods of producing the biogel nanosensors, and methods of using the biogel nanosensors.

1. Biogel Nanosensor for Detecting an Analyte

One aspect of the disclosed technology is a biogel nanosensor for detecting an analyte in a sample comprising an acryloyl or a methacryloyl modified hydrogel on the surface of a substrate, and nucleic acid amplification reagents, in which the hydrogel is crosslinked in picoliter or nanoliter volume on the surface of the substrate in a microarray form of spots, and the nucleic acid amplification reagents are combined, added, or applied in picoliter or nanoliter volume to the hydrogel spots after crosslinking. The term "spots" refers to a microarray or form of an ink jet print. The terms "microarray" or "microarray chip" or "microarray spots" are used interchangeably herein.

An acryloyl or a methacryloyl modified hydrogel is a modified gelatin with respect to free amino groups, for example modified with an acryloyl group (using for example acrylic anhydride or glycidyl acrylate) or a methacryloyl group (using for example methacrylic anhydride). An acryloyl or a methacryloyl group at a previous amino group is crosslinkable. Generally, the lower the degree of modification (lower excess of reagent), the more viscose is the printing solution (bioink). In all embodiments of the biogel nanosensor and the disclosed methods of making and using the nanosensor, an acryloyl hydrogel is identified as "GAcry", and "GAH," and a methacryloyl hydrogel is identified by "GM." The degree of modification is identified by a suffix denoting the molar excess of the reagent used with respect to free amino groups. For example, an acryloyl hydrogel may be identified as GAcryl1, GAcryl2, and so forth, and GAH1, GAH2, and so forth. A methacryloyl hydrogel may be identified as GM1, GM2, and so forth. Thus, the higher the degree of modification, the more crosslinkable groups.

In all embodiments, a methacryloyl hydrogel may further be modified with acetyl groups (using for example acetic anhydride), which are non-reactive masking groups. In the embodiments, a methacryloyl hydrogel is acetylated to form a methacryloyl acetylated hydrogel, identified by "GM" and "A" with the degree of modification as a suffix. In some embodiments, the methacryloyl acetylated hydrogel is identified as $GM_2A_8$, or $GM_{10}A_{10}$, for example. Another modification of a methacryloyl hydrogel is cationized with ethylene diamine, which may also be used in the disclosed biogel nanosensors and related methods. A methacryloyl ethylene diamine is identified by "GM" and "E" for the modified hydrogel, with the degree of modification as a suffix. An exemplary methylacryloyl ethylene diamine hydrogel with 10-fold molar excess of modified gelatin to free amino groups and ethylene diamine to carboxy groups, designated as $GM_{10}E_{10}$, may be used in the disclosed biogel nanosensors. In addition, a methacryloyl hydrogel may be modified with an acetyl group and ethylene diamine, for example $GM_{10}A_8E_{10}$.

In further embodiments, combinations or mixtures of the modified hydrogels may be used, for example GM2/GMS. In some embodiments, a modified hydrogel disclosed herein is an acryloyl hydrogel, a methacryloyl hydrogel, or combinations thereof. In some embodiments, the modified hydrogel is an acryloyl hydrogel. In some embodiments, the modified hydrogel is a methacryloyl hydrogel, a methacryloyl acetylated hydrogel, a methacryloyl ethylene diamine, or combinations thereof.

In embodiments, the total volume of hydrogel and nucleic acid amplification reagents for each spot on the microarray is in the range of about 0.1 nL to about 10 nL. In some embodiments, the volume is in the range of about 1 nL to about 5 nL. In some embodiments, the volume of hydrogel and amplification reagents is 5 nL. In embodiments, the volume of hydrogel for a spot in the microarray is obtained from about 50 pL to about 500 pL drops of the hydrogel to a spot. In embodiments, the volume of hydrogel for a spot in the microarray is obtained from 50 pL to 500 pL drops of the hydrogel to a spot. In embodiments, the volume of the nucleic acid amplification reagents is obtained from about 50 pL to about 500 pL drops of the reagents to a spot.

In embodiments, the nucleic acid amplification reagents are combined, added, or applied in picoliter or nanoliter volume to the hydrogel spots after crosslinking. In the embodiments, combining, adding or applying nucleic acid amplification reagents includes layering the reagents on the crosslinked hydrogel. In some embodiments, the nucleic acid amplification reagents are layered on the crosslinked hydrogel spots. For example, the nucleic acid amplification reagents may be layered on the crosslinked hydrogel spots after the hydrogel is crosslinked on the substrate surface. In some embodiments, the nucleic acid amplification reagents are combined with the hydrogel prior to crosslinking on the substrate surface.

In embodiments, the nucleic acid amplification reagents provide for nucleic acid amplification to detect the analyte in the sample. Any nucleic acid amplification protocol may be useful with the disclosed biogel nanosensor. Examples of nucleic acid amplification include isothermal amplification, polymerase chain reaction, clustered regularly interspaced short palindromic repeat amplification, ligation mediated amplification, strand displacement amplification, ligase chain reaction, nucleic acid based sequence amplification. In embodiments, the nucleic acid amplification is isothermal amplification, for example loop-mediated isothermal amplification (LAMP), strand displacement amplification, multiple-displacement amplification, rolling circle amplification, and transcription mediated amplification.

In all of the embodiments, the nucleic acid amplification reagents include DNA or RNA, at least one primer, at least one polymerase, at least one reverse transcriptase, at least one amplification buffer, at least one deoxynucleoside triphosphate (dNTP), reagents, and at least one detection element. In some embodiments, the reagents include a mixture of dNTPs. In some embodiments, the reagents contain Mg ions, for example $MgSO_4$. In embodiments, the detection element is a fluorescent, colorimetric, or electrochemical element. In some embodiments, the detection element is a dye or fluorophore. In embodiments, the at least one primer includes loop primers.

Nucleic acid amplification reagents, such as LAMP reagents are usually stored at −20° C. for preserving their efficiency, which necessitates a cold chain requirement for any field deployment of a diagnostic LAMP assay. An advantage of the disclosed biogel nanosensor is the ability to remain stable at room temperature for a long period of time. In embodiments of the disclosed biogel nanosensor, the nucleic acid amplification reagents are stable at room temperature of about 22° C. to about 37° C. In some embodiments, the biogel nanosensor remains stable at a temperature range of about 22° C. to about 37° C. for at least 30 days.

Any substrate that will provide for a microarray or forming a microarray with a hydrogel may be useful for the disclosed biogel nanosensor and related disclosed methods. In some embodiments, the substrate is selected from glass, plastic, polymer, adhesive tape, paper, titanium, and combinations thereof. In some embodiments the substrate is glass. In some embodiments the substrate is a polymer, such as a polymer film. In some embodiments, the substrate is adhesive tape. In some embodiments the substrate is a plastic, such as oriented polypropylene (OPP), polyethylene terephthalate (PET), polyether sulfone (PES), and polydimethylsiloxane (PDMS). In some embodiments, the substrate is paper, such as filter paper, silanized paper, or hydrophobic paper.

In embodiments, the substrate surface may be functionalized or coated with a polymer. In some embodiments, substrate surface is functionalized with a charge, or is plasma functionalized. In some embodiments, the polymer in the form of a liquid, film, or sheet. In some embodiments, the polymer is 3-(trimethoxysilyl) propyl methacrylate (TMSPMA). In some embodiments, the substrate is coated or functionalized oriented polypropylene (OPP), polyether sulfone (PES), or polyethylene terephthalate (PET). In other embodiments, the substrate surface is not coated or functionalized.

A light guide provides an intensity of light for crosslinking a hydrogel. In embodiments, the biogel nanosensor further comprises a light guide. In embodiments, the light guide may be layered on top of the hydrogel and the amplification reagents, such as in a film or laminated film. In embodiments, the light guide may be in a translucent polymer film that is layered over the microarray, for example as a top of the biogel nanosensor. In some embodiments, the light guide emits light from a biogel nanosensor to a detection array (such as a charge coupled device (CCD)). In embodiments, the light guide is a light emitting diode (LED) or an ultraviolet light.

In some embodiments, the light guide provides an intensity of light that is in the range from about 4 $mW/cm^2$ to about 12 $mW/cm^2$. In some embodiments, intensity of light is in the range from about 4 $mW/cm^2$ to about 9 $mW/cm^2$, more particularly the intensity of light is in the range from about 4.4 $mW/cm^2$ to about 9 $mW/cm^2$, more particularly about 4.4 $mW/cm^2$ or about 9 $mW/cm^2$.

Heating elements are commonly used in an amplification assay for initiation of amplification. Any known heating element effective for an amplification assay may be used with the disclosed biogel nanosensor. In embodiments, the biogel nanosensor comprises a heating element. In some embodiments, the heating element is in the nanosensor. In embodiments in which the heater is in the nanosensor, the heater is an ultrathin heater. In some embodiments, the heating element is connected to the nanosensor, such as through an external device. In some embodiments, the heating element is a module of an analyzer device used for analyzing a biogel nanosensor, including in a method analyzing nucleic acid amplification using the disclosed biogel nanosensor.

Current processes for nucleic acid amplification assays often require a pump or pump-type aspect to deliver a sample to the amplification assay reagents. Such pumps are not conducive to a rapid and simple point-of-care device. In embodiments of the disclosed technology, the biogel nanosensor further includes a wicking matrix. The wicking matrix may be applied over the biogel nanosensor microarray to deliver a sample to the biogel nanosensor microarray without the need for a pump. The wicking matrix may be paper, which may draw the sample into the biogel nanosensor and deliver the sample to the hydrogel with the nucleic acid amplification reagents (hydrogel array).

In all aspects of the disclosed technology and methods, a sample may be from any source that contains nucleic acid. In some embodiments, the samples may be from human, animal, plant, or environmental sources. In embodiments, the sample may be a biological sample obtained from a human subject. Exemplary biological samples include, but are not limited to, saliva, sweat, blood, serum, plasma, cell lysate, milk, vitreous fluid, and other secretions, and cells and tissue such as a homogenate. In some embodiments, the sample for detection of an analyte is a bodily fluid, including sweat, saliva, blood, plasma, and serum. In some embodiments, the sample is a non-biological fluid, such as from environmental sources or ecological environments such as a river, stream, lake, ocean, or drinking water supply, or laboratory solution. Moreover, the sample can be in various forms including but not limited to a liquid, homogenized, frozen, chilled, or lyophilized sample. The sample may be subjected to additional treatment or purification steps prior to the biogel nanosensor detection described herein.

In all aspects of the disclosed technology, the analyte for detection may be from any source containing ribonucleic acid that may be amplified. In embodiments, the analyte for detection may be a virus, bacteria, fungi, protozoa that contains ribonucleic acid, or deoxyribonucleic acid or other polymer comprised of standard and nonstandard bases (nucleobases, nitrogenous bases). Examples of viruses in some embodiments include influenza virus, Rhinovirus, dengue virus, Zika virus, Japanese encephalitis virus, Chikungunya virus, SARS-CoV virus, and Sindbis virus.

A biogel sensor disclosed herein is not limited to detecting one analyte or one type of analyte. The microarray format of distinct spot allows for spacial multiplexing, that is more than one test may be printed in an array among the printed spots. In embodiments for the biogel nanosensor and methods of making the nanosensor, the nucleic acid amplification reagents may be directed to the same analyte on each hydrogel spot. Similarly in the embodiments, the nucleic acid amplification reagents may be directed to different analytes. By way of example, the nucleic acid amplification reagents may contain primers directed to different analytes. In certain embodiments, nucleic acid amplification reagents layered on one hydrogel spot are directed to a first analyte, and nucleic acid amplification reagents layered on a second or separate hydrogel spot are directed to a second analyte, different from the first analyte. Thus, it is possible in one embodiment that the nucleic acid amplification reagents layered on each hydrogel spot in the microarray may be directed to different analytes. In some embodiments, the nucleic acid amplification reagents layered on the hydrogel spots in one row (for example, a first row) of the microarray may be directed to one analyte, and the nucleic acid amplification reagents layered on the hydrogel spots in a second or separate row within the microarray may be directed to a second, separate analyte. In the embodiments, nucleic acid amplification reagents directed to separate analytes is limited only by the number of hydrogel spots in the microarray.

Current point-of-care (POC) detection devices use various techniques, such as advanced microfluidics, nanomaterials, and microarray technology that can be expensive to implement and can create barriers in field implementation. Here, inkjet printing was adapted to be compatible with large scale manufacturing and roll-to-roll processing to develop a platform that can sensitively detect RNA. An inkjet printing approach to a simple and robust nucleic acid amplification assay was accomplished by integrating it with an acryloyl or a methacryloyl modified hydrogel. A reduction in total reaction volume from previously published assays was demonstrated with improved sensitivity. The amplification assay was optimized and characterized for in-tube and ink-jet printing, providing reduced volume setup with the limit of detection at $10^3$ copies per reaction, which was well below the previously known range of RNA loads.

The disclosed biogel nanosensor is an efficient point of care NAAT device that provides detection of a vast array of analytes rapidly without temperature constraints. The disclosed biogel nanaosensor provides multiplexed nucleic acid amplification assay in picoliter or nanoliter volume in a compact module. The biogel nanosensor overcomes the disadvantages of the flawed or incompatible systems that do not function as real point-of-care tests. Unlike the prior art, the disclosed biogel nanosensor is discretized with small volume of amplification components in a hydrogel that is compact, stable for an extended period without the need for cold storage, and sensitive for a multitude of analytes. A sample may be applied simply at a true point-of-care or point-of-infection point. When combined with real-time, compact detection devices, such as smartphone technology, a rapid detection system is available that allows simultaneous analysis and quantification of an analyte, and diagnosis of an infection.

2. Preparing a Biogel Nanosensor

Another aspect of the disclosure is a method of preparing a biogel nanosensor that includes obtaining an acryloyl or a methacryloyl modified hydrogel, applying the hydrogel in picoliter or nanoliter volume on the surface of a substrate in a microarray in the form of spots, crosslinking the hydrogel on the substrate surface, and combining or adding or applying nucleic acid amplification reagents in picoliter or nanoliter volume to the crosslinked hydrogel.

In embodiments, hydrogel and nucleic acid amplification reagents are applied to the substrate using inkjet printing or screen printing. In embodiments, inkjet printing applies or delivers or "prints" each of the hydrogel and nucleic acid amplification reagents as droplets (drops or dots) in picoliter volumes to each spot of the microarray. In some embodiments, the inkjet printing prints 50 pL to 500 pL drops of hydrogel and/or nucleic acid amplification reagents to each spot of the microarray.

In embodiments, the hydrogel and nucleic acid amplification reagents are applied to each spot on the microarray in a total volume in the range of about 0.1 nL to about 10 nL. In some embodiments, the volume is in the range of about 1 nL to about 5 nL. In some embodiments, the volume of hydrogel and amplification reagents is 5 nL. In embodiments, the hydrogel and nucleic acid amplification reagents, that is the total amount of all of the reagents, are applied in about equal volumes.

In some embodiments, the method further comprises adding a light guide to the biogel nanosensor. In embodiments, the light guide is layered on the crosslinked hydrogel and amplification reagent microarray. In some embodiments, the light guide is in a sheet that covers the crosslinked hydrogel and amplification reagent microarray. In some embodiments, the light guide is in a sheet that forms a cover for the biogel nanosensor. In embodiments, the sheet containing the light guide is formed of a translucent plastic film.

The light guide provides an intensity of light for crosslinking the hydrogel. The light guide can also emit light from a biogel nanosensor to a detection array (such as a charge coupled device (CCD)). In all of the described embodiments, the light guide is a light emitting diode or an ultraviolet light. In all of the described embodiments, the light guide provides an intensity of light that is in the range from about 4 mW/cm$^2$ to about 12 mW/cm$^2$. In some embodiments, intensity of light is in the range from about 4 mW/cm$^2$ to about 9 mW/cm$^2$, more particularly the intensity of light is in the range from about 4.4 mW/cm$^2$ to about 9 mW/cm$^2$, more particularly about 4.4 mW/cm$^2$ or about 9 mW/cm$^2$.

In some embodiments, the method further comprises adding a heating element to the biogel nanosensor. Any known heating element effective for initiating an amplification assay may be used in the disclosed method for making the biogel nanosensor. In embodiments, the heating element may be added within the biogel nanosensor. In embodiments in which the heater is in the nanosensor, the heater is an ultrathin heater. In some embodiments, the heating element is connected to the nanosensor externally, such as through an external device. In some embodiments, the heating element is a module of an analyzer device used for analyzing a biogel nanosensor, including in analyzing nucleic acid amplification using the disclosed biogel nanosensor.

3. Methods of Using the Biogel Nanosensor

A further aspect of the disclosure is a method of detecting an analyte in a sample, comprising contacting a biogel nanosensor described herein with a sample; and measuring the presence of a detectable signal produced by the analyte in the sample.

In embodiments, the biogel nanosensor comprises a light guide. In some embodiments, the light guide is a light emitting diode or an ultraviolet light. In some embodiments, the light guide crosslinks the hydrogel on the substrate surface.

In embodiments, contacting the biogel nanosensor with a sample includes applying a sample to the nanosensor. In some embodiments, the sample is in a form to make contact with each of the spots in the microarray. In some embodiments, the sample is a liquid that flows across hydrogel and amplification reagent spots. In some embodiments, the biogel nanosensor comprises a wicking matrix that wicks the sample to the hydrogel and nucleic acid amplification reagents on the microarray spots. In embodiments, the sample contacts the crosslinked hydrogel and nucleic acid amplification reagent spots with a wicking matrix. In the embodiments, the wicking matrix is paper layered over the microarray in the biogel nanosensor.

In some embodiments, measuring the presence of a detectable signal comprises applying a heating element to the biogel nanosensor after contact with the sample. In embodiments, the heating element is applied to the biogel nanosensor as a further element within the biogel nanosensor. In other embodiments, heating element is connected externally to the biogel nanosensor. The heating element may be connected externally to the biogel nanosensor through a wire or cable, or the biogel nanosensor is connected to an external analyzer that contains the heating element.

In embodiments, the heating element or heater is activated and initiates amplification assay with the sample and the nucleic acid amplification reagents. In some embodiments, the heater element heats the biogel nanosensor to a range of about 63° C. to about 70° C. for a time sufficient for amplification to be detected. In embodiments, the sample contains at least one analyte that is detectable by a detection element in the nucleic acid amplification reagents, and the at lease one analyte in the sample is detected.

In some embodiments, the method uses nucleic acid amplification reagents that are directed to one analyte or one type of analyte. In some embodiments, the nucleic acid amplification reagents may be directed to different analytes. In some embodiments, the nucleic acid amplification reagents on each hydrogel spot are directed to the same analyte. In other embodiments, the nucleic acid amplification reagents on one hydrogel spot may be directed to different nucleic acid amplification reagents on a second or separate hydrogel spot. By way of example, the nucleic acid amplification reagents may contain primers directed to different analytes. In certain embodiments, nucleic acid amplification reagents layered on one hydrogel spot have a primer directed to a first analyte, and nucleic acid amplification reagents layered on a second or separate hydrogel spot have a primer directed to a second analyte, different from the first analyte. Thus, in some embodiments that the nucleic acid amplification reagents layered on each hydrogel spot in the microarray may be detecting different analytes. In some embodiments, the nucleic acid amplification reagents layered on the hydrogel spots in one row (for example, a first row) of the microarray may be directed to one analyte, and the nucleic acid amplification reagents layered on the hydrogel spots in a second or separate row within the microarray may be directed to a second, separate analyte. Therefore, the method may be detecting more than one analyte in one assay or text. In the embodiments, nucleic acid amplification reagents directed to separate analytes is limited only by the number of hydrogel spots in the microarray.

In one embodiment, the method of detecting an analyte in a sample includes connecting the biogel nanosensor to an analyzer or reading device for detecting and quantifying the analyte. A portable reader may be used for detection of the amplification product. The reader could be a standalone device with a heating unit, an optical detection system (e.g. fluorescence), data acquisition capability, and preferably, a graphic user interface. The standalone reader may be compatible with a smartphone for some of those capabilities. Alternatively, a smartphone may be the reader device, which would have an analyzer capability or application.

Modules or elements of a reader or analyzer device may include a housing, a frame, a heating module, a detection unit (such as camera and fluorescence/colorimetric submodules), a control element (microcontroller or other device that can control the whole system). The reader may contain a display or may be connected to display module such as a smartphone.

The reader may accept the biogel nanosensor (POC test chip) directly, in which case the analyzer reader would initiate amplification, detect the results of amplification is any, and identify an analyte from a detectable signal, for example, from the spots on the microarray.

The described technology is further illustrated by the following examples which in no way should be construed as being further limiting.

EXAMPLES

Materials and Methods
DNA Stocks and RNA Translation

The dengue virus (DENV) target sequence first reported by Lau, et al. (2015) that codes for the 3'NCR sequence of DENV-1 Western Pacific strain (Genbank: U88535.1) was used. The nucleotide sequence was purchased (GenScript) cloned in a pcDNA3.1 plasmid. Standard heat shock transformation was used to insert the plasmid into NEB® 5-alpha Competent *E. coli* cells (NEB). The control DENV-1 plasmid was extracted using a QIAprep® Spin Miniprep Kit (Qiagen). The DENV-1 plasmid was linearized with SmaI (NEB) prior to downstream usage. For reverse transcription (RT)-LAMP assays, the linearized DENV-1 plasmid was reverse transcribed and purified following instructions on MEGAscript™ Transcription Kit (Invitrogen) and MEGAclear™ Clean-Up Kit (Invitrogen).

The quality of purified DNA/RNA was estimated and quantified via NanoDrop™ 2000C Spectrophotometer (ThermoFisher Scientific). The DENV-1 DNA plasmid used is 5624 bp in length, which corresponds to a molecular weight of about 3475 kDa. Along with the concentration of plasmid (ng/μL), an estimated 6.15 pg of target corresponds to $10^6$ copies. The transcribed RNA product is long and has a molecular weight of 451 kDa. An estimated 74.4 pg of DENV RNA target corresponds to $10^6$ copies.

Sensitivity and Specificity of DENV RT-LAMP Assay with QUASR Detection

A quenching of unincorporated amplification signal reporters (QUASR) LAMP assay was adapted from Meagher, et al. (2018), which reported optimized primer sets for targeting DENV-1 compatible with the QUASR technique. All primer sequences used are listed in Table 1.

TABLE 1

Complete set of primers used for DENY RT-LAMP assay

| Primer name | Sequence |
| --- | --- |
| DENV-1 F3 | TGGGGTAGCAGACTAGTGG (SEQ ID NO. 1) |
| DENV-1 B3 | TCTGTGCCTGGAATGATGC (SEQ ID NO. 2) |
| DENV-1 FIP | CCACCAGGGTACAGCTTCCC GACCCCTCCCAAAACACAA (SEQ ID NO. 3) |
| DENV-1 BIP Cy5- | Cy5-AGAGGTTAGAGGAGACCCCCC CAGGATCTCTGGTCTCTCCC (SEQ ID NO. 4) |

TABLE 1-continued

Complete set of primers used
for DENY RT-LAMP assay

| Primer name | Sequence |
|---|---|
| DENV-1 LoopF | TGGTGTTGGGCCCCGCT (SEQ ID NO. 5) |
| DENV-1 LoopB | AAACAGCATATTGACGCT (SEQ ID NO. 6) |

Underlined sequences within the forward inner primer (FIP) and backward inner primer (BIP) reflect the F1c and B1c regions of those primers.

RT-LAMP reactions were either carried out in 8 strip PCR tubes or 96-well plates with 1 µL of template and 4/9 µL of master mix solution. The fresh master mix solutions (optimized concentrations) were prepared with 1× Isothermal Amplification Buffer (20 mM Tris-HCl, 10 mM $(NH_4)_2SO_4$, 50 mM KCl, 2 mM $MgSO_4$, 0.1% Tween® 20, pH 8.8 @ 25° C., NEB), 1.4 mM of each nucleotide (dNTP mix, NEB), 8 mM $MgSO_4$ (NEB), 1×CYGREEN Nucleic Acid Dye (Enzo), 0.6 µM each F3 an dB3, 0.8 µM each LF and LB, 4.8 µM each FIP and Cy5 labelled BIP and 7.2 µM of quencher primers (Table 1), 1.6 units of WarmStart® RTx Reverse Transcriptase (NEB), and 3.2 units of Bst 2.0 WarmStart® DNA Polymerase (NEB). Remaining volume in the reaction was made up with nuclease free water (NEB) or with 57.91% (w/v) of $GM_{10}$ for a final concentration of 10% (w/v) in case of hydrogel based RT-LAMP. Samples were incubated at 65° C. for 50 minutes in a thermocycler or a hotplate (Eppendorf). Limit of detection studies were performed using serially diluted RNA ($10^6$-$10^0$ copies per reaction). For specificity study, equal amounts of both Zika virus (ZIKV) and DENV RNA were used ($10^6$ copies per reaction) at the same conditions as above.

For real-time monitoring of the reaction, fluorescent intensity was collected every one minute through FAM channel during incubation at 65° C. for 50 minutes and then reaction was brought down to 25° C. for 5 minutes and fluorescent intensity was again measured though Cy5 channel using QuantStudio5 thermocycler (ThermoFisher Scientific).

Gel Electrophoresis and Imaging for Target

Gel electrophoresis was used to analyze success of DENV plasmid purification, linearization of DENV plasmid and resulting LAMP products. For longer DNA-like plasmids, 1.5% agarose gel poured in house were run with 1×TBE buffer (VWR). 5 µL of plasmid with 6× loading dye (NEB) were added per well and gels were run for 1.5 hours at 150 V. For analyzing LAMP products, 6% Novex® pre-cast TBE Gels (Invitrogen) were run following manufacturer specifications for 1 hour at 90 V. All gels were stained after completion of run with SYBR green for 30 mins and imaged with a Versadoc Imager (BioRad) or a UV trans-illuminator (Invitrogen).

All RT-LAMP assays both in tube/plate and on chip were imaged at end point with an inverted fluorescence microscope (Olympus IX-70, Center Valley, PA) for the acquisition of the fluorescence images. Cy5 fluorescence measurement was done at an excitation wavelength of 635 nm. Each image covered a 250-µm by 250-µm area of the sample. Image data was collected by a monochrome CCD camera (Hammatsu, Japan).

Hydrogel Preparation and Inkjet Printing

Freeze dried hydrogels ($GM_{10}$ and $GM_2A_8$; the suffix denotes the molar excess of the reagent used with respect to free amino groups) in sealed packets were obtained from Fraunhofer IGB (Hoch, et al., 2012). To crosslink and dissolve the gel, required weight of freeze dried gels were dissolved in nuclease free water containing 1% (w/v) of Irgacure-2959 (Sigma) at 80° C. After dissolving, gels were quickly spun and filtered via 0.2 µm syringe filters.

For inkjet printing, filtered hydrogel was dispensed in 500 pL droplets at defined spots onto a target substrate using a piezoelectric noncontact printer (SciFLEXARRAYER S3, Scienion AG, Berlin, Germany). Spotted substrates were dried for 10 mins inside the humidified chamber before being transported to be UV crosslinked. For printed RT-LAMP reactions, the reaction mix mixed with template was dispensed using the above printer at the same location of the hydrogel and transferred to a sealed well plate for heating.

Hydrogel Adherence and Glass Substrate Treatment

Standard glass slides were cleaned with 100% ethanol via sonication for 30 minutes, followed by 30 minutes of sonication with homemade nuclease removal solution (10% bleach, 10% NaOH, 1% Alconox®) and another 30 minutes of sonication with nuclease free water. After slides were dried with a compressed air gun, they were treated with 1% (v/v) 3-(trimethoxysilyl) propyl methacrylate (TMSPMA) (Sigma) in methanol for 30 minutes. Any unbound TMSPMA was rinsed off with 100% ethanol and let to oven dry at 37° C. before use.

For adherence tests, 1 µL of prepared hydrogel was pipetted onto the treated glass slide in discrete spots and then crosslinked by UV with a peak wavelength of 365 nm for specified intensity and time. After crosslinking, slides were immersed in 1×PBS (VWR) for one hour and number of adhered spots were recorded. The optimized crosslinking time used for downstream assays was 2 minutes at an intensity of 9 mWcm-2.

Hydrogel Reagent Storage

5 µL of freshly prepared hydrogels were pipetted into PCR tubes and UV cured for 2 minutes at an intensity of 9 $mWcm^2$. 2.13 µL of reaction mix-1 containing only the primers, dNTPS, polymerase and dyes were added on top of the hydrogels in tubes, spun and dried in laminar air flow for 30 minutes. Prepared tubes were then sealed in sterilized pouches and stored at either room temperature or at 37° C. away from light for required amount of time. To reconstitute the reaction, 1.87 µL of reaction mix-2 containing only Isothermal Amplification Buffer and $MgSO_4$ (source of Mg++ ions) were added to each tube along with 1 µL of template and 2.13 µL of nuclease free water to make up the volume to 5 µL. Tubes were given a quick spin before running them on the thermocycler.

Device Fabrication

Acrylic sheets of 1.5 mm thickness (McMaster-Carr) and double sided adhesive tape (ARseal™ 90880), were laser cut by an Epilog Zing laser cutter (35 W) per the input CAD drawing. The cutting parameters for 1.5 mm thick acrylic sheets were 30% speed, 50% power and 500 Hz frequency. For the double sided adhesive tape, cutting parameters were 80% speed, 5% power and 500 Hz frequency. All device materials were rinsed with 100% ethanol and homemade RNAase AWAY. After device materials were air dried, they were assembled by carefully by aligning the layers of acrylic sheets and tape. The cover of the device was attached once the hydrogels containing the RT-LAMP assay reagents were added to the wells and crosslinked. The sample was added manually via a 100 µL pipette tip.

Statistical Analyses

The limit of detection was determined as the lowest DNA/RNA concentration that yielded 100% amplification rates detectable by Cy5 fluorescence in all three replicate trials. A reaction was considered positive if the average Cy5 fluorescent intensity was twice as intense as the corresponding negative control. This threshold was set by observing trends in real time plots. Chips and benchtop reactions with detectable Cy5 fluorescence in no template controls were removed from analysis due to possible contamination in the common reaction mix. All microscopic images were analyzed with ImageJ (NIH). Any fluorescent intensity measurements were measured using inbuilt ImageJ functions. Real time LAMP plots and Cy5 fluorescence intensity measurements for in tube assays were recorded via the QuantStudio™ (ThermoFisher) software. All plots were graphed using Microsoft Excel (Microsoft). All figure preparations were done using Inkscape™.

Example 1

Nucleic Acid Amplification Assay Development

Standard RT-PCR assays are harder to implement in low resource settings to detect viral infections. Instead of requiring precision equipment for thermal cycling for amplification of DNA/RNA, the LAMP technique can amplify a few copies of DNA to $10^9$ in less than an hour under isothermal conditions and with greater specificity. This increased specificity is due to the fact that LAMP uses six sets of primers to target six distinct sequences initially and then by four distinct sequences onwards. (Notomi, et al. 2000).

Figure 4:
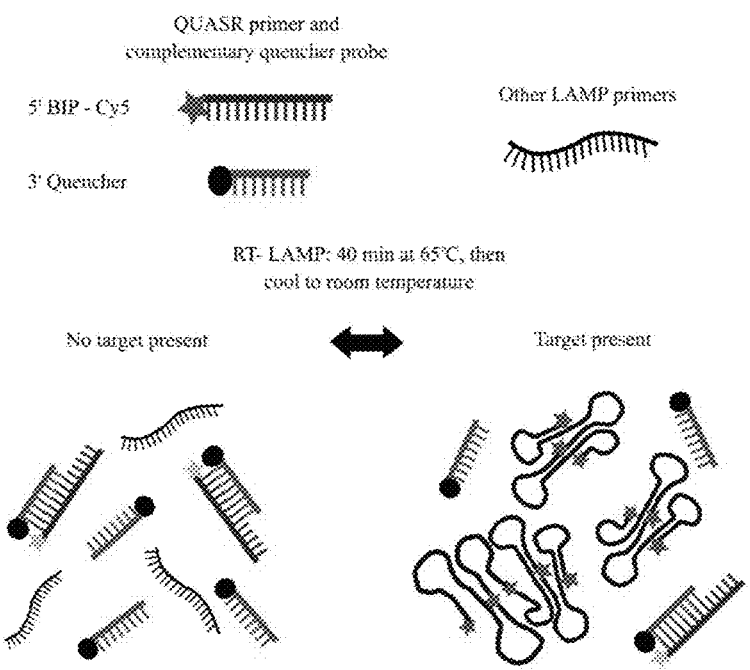
FIG. 4: Principle of QUASR detection in RT-LAMP by Ball, et al., 2016. The reaction mixture has one of the inner primers (FIP or BIP) labeled with a fluorescent dye and a short complementary quencher probe which is in relative excess. As reaction cools down to room temperature, the unincorporated fluorescent primers are quenched while amplicon remain highly fluorescent due to incorporated primers.

However, one of the common drawbacks of LAMP is the lack of suitable closed tube detection techniques. The color changes in a colorimetric closed tube detection LAMP-based assay may be too subtle to detect. Other nucleic acid binding dyes require elevated temperatures for distinction between positive and negative samples. Here, a QUASR detection technique (Ball, et al. 2016), which enables closed tube fluorescent detection of specific amplicons was adapted for LAMP assay. The QUASR technique relies on introduction of a fluorescent reporter at the 5' end of one of the LAMP primers (usually FIP) and also the incorporation of a short 3' complementary quencher probe. The quencher probe is designed to be dissociated during amplification so that it doesn't interfere with amplification or bind to the complementary primer. As the temperature of the reaction drops down after the amplification run, the quencher probe binds to any free labelled primer present that has not been incorporated in the amplicon. This results in the quenching of the fluorescent probe on the primer. However, the incorporated labelled primer results in fluorescently tagged amplicons that can be detected upon laser excitation (FIG. 4). This technique allows distinction between positive and negative tubes by clearing out any excess fluorescence and recognizing target amplicons (Ball, et al. 2016).

The DENV QUASR RT-LAMP assay developed by Meagher, et al. (2018) was adapted in the new platform disclosed herein, in which primer and reagent concentrations present in the reaction mix were optimized along with the establishing a reduced volume setup, assay sensitivity, and specificity to common symptomatic diseases. An assay was considered optimized if the limit of detection was below the range of clinically reported DENV loads in serum.

The volume of the reaction was reduced by half without affecting the lowest detection limit (shown in a LAMP assay with DNA target). A reduction in volume also resulted in a decrease of time to positivity (Ct). By increasing the inner primer concentrations and adjusting Mg++ ions, $10^3$ copies per reaction or more were detected. This detection limit is suitable for diagnosing infections in dengue hemorrhagic fever (DHF) and dengue fever (DF) on day 3-4 of illness when viral loads in serum are higher than detection limit (Teoh, et al. 2015). The specificity of the optimized assay was confirmed for DENV against other closely related viruses.

Reduced Volume Setup of DENV LAMP Assay

Figure 5:
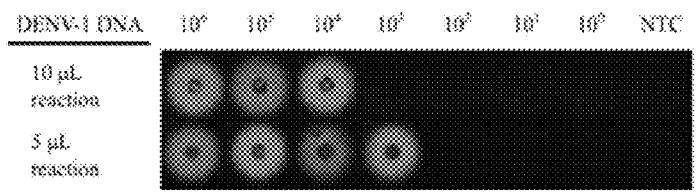
FIG. 5: Reduced volume RT-LAMP assay. The top row shows the endpoint fluorescent readout in Cy5 channel for respective wells after amplification cycles have ended (n=3). The observed limit of detection increased 10 fold when the total reaction volume was decreased by half.

For the proposed new platform to incorporate nanoliter LAMP reactions the effects of reducing total reaction volume was investigated. Reducing the volume of a LAMP reaction can affect the efficiency of amplification and in some cases either decrease or increase the limit of detection (Gaines, et al. 2002). Following the reaction mix listed in Meagher, et al. (2018), the LAMP assay was run with DENV DNA target for an end point readout in two volume setups, one being 10 µL (standard) and other 5 (lowest possible volume to ensure reliable pipetting). FIG. 5 shows the fluorescent end point readout of this assay with serially diluted copies of DNA target ranging from $10^6$ copies per reaction to 1 copy per reaction. With a reduced volume setup (5 µL), a 10 fold increase in limit of detection (n=3) was observed. From the real time plots, lower Ct values were observed for the reduced volume setup (Table 2). This may be due to increased interaction of primers and target and subsequent self-priming LAMP amplicons. Thus, reducing volume could help increase limit of detection as well as decrease time to positivity. Table 2 below shows values obtained from real time DENV LAMP assay on the QuantStudio (n=3) for the lowest concentration of DNA target that resulted in a positive readout. By reducing the volume in half, the time to positivity was also reduced in half. Ct values were not significantly different for higher concentrations of DNA ($10^6$ copies) when volume of the reaction was reduced.

TABLE 2

Effect of reduction of reaction volume on time to positivity (Ct) values for DENV LAMP assay.

| Ct values for 5 µL DENV LAMP $10^4$ copies (in mins) | Ct values for 10 µuL DENV LAMP $10^4$ copies (in mins) |
|---|---|
| 12.0623 | 24.660 |
| 12.344 | 23.492 |
| 12.023 | 22.058 |

RT-LAMP Assay Sensitivity and Limit of Detection in Tube

Figure 6A:
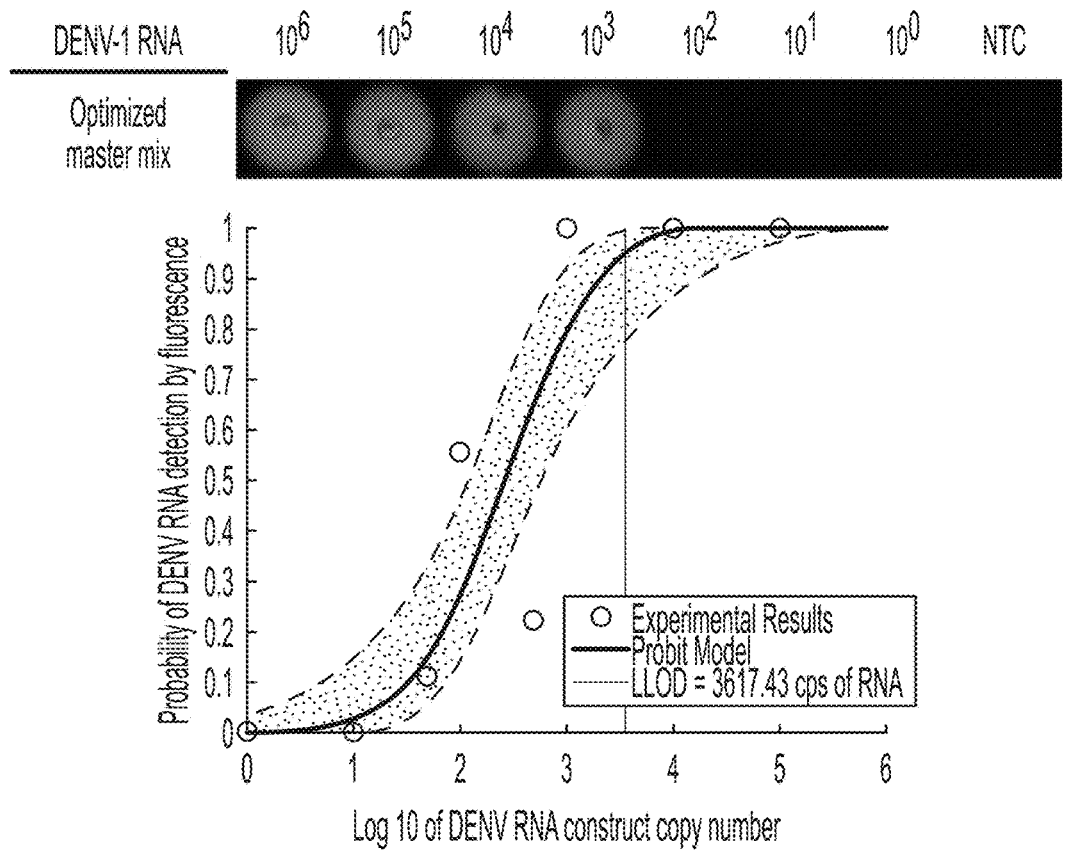
FIGS. 6A-6B show the limit of detection of DENV RT-LAMP assay.
Figure 6B:
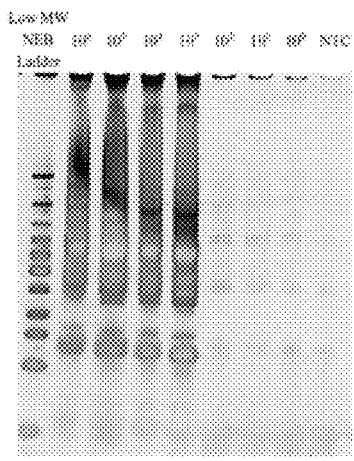

To develop a robust RT-LAMP assay that would result in a clear readout between positive and negative DENV samples while still detecting low viral concentrations in clinical samples, whether the assay limit of detection was below reported clinical viral loads. The clinical DENV RNA loads found in serum of infected patients range from as low as $10^4$ copies/mL to about $10^{12}$ copies/mL (Gurukumar, et al. 2009). With the current RT-LAMP master mix even $10^3$ copies per reaction were not detected in 100% of trials (3 positive in 6 cases) and hence the assay conditions were optimized further by modifying concentrations of primers and Mg++ ions such that detection reached around 10 copies per reaction (equivalent to $10^4$ copies per mL). The inner primers are involved in the initial stages of the amplification cycle and are necessary in binding to target and creating amplicons that self-initiate amplification (Notomi, et al. 2000). The concentration of primers was increased 1.5× times and concentration of Mg++ ions was increased to 10 mM ($MgSO_4$ buffer added to the master mix to take the final concentration of Mg++ ions to 10 mM). Results from this assay are shown in FIG. 6A. Gel electrophoresis analysis of products is shown in FIG. 6B.

The lowest concentration that indicates Cy5 fluorescence in 100% of trials is reported as the limit of detection. Increasing the primer concentration resulted in a detection limit of $10^3$ copies per reaction (n=9). Also, $10^2$ copies per reaction were detected in 55% of trials. The probit model predicts the limit of detection with 95% positivity to be $3.6\times10^3$ copies per reaction. Even though lowest reported loads were not detected, the limit of detection was well below the mean viral loads reported in early days of infection (greater than $10^4$ copies per reaction on day 3). The RT-LAMP reaction mix recipe was finalized for subsequent reactions and the limit of detection increased by incorporating the hydrogel in the assay.

The effect of betaine in reaction mix was also tested. Betaine has been reported in some cases to improve amplification efficiency and decrease threshold times (Wang, et al. 2015). However, that was not the case in the disclosed assay setup that showed a lower amplification rate with betaine.

To further verify the chosen conditions, the temperature of the reaction was varied to the range of 63° C. and 70° C. The results showed the temperature range was effective, with 65° C. being an optimal temperature.

Assay Selectivity Against Other Common Viruses

To confirm selectivity for DENV specific 3' NCR region, the RT-LAMP assay was tested against other viral infections Zika virus (ZIKV), Japanese encephalitis virus (JEV), Chikungunya virus (CHIKV), and Sindbis virus (SINV) that have similar symptoms to DENV and can confound diagnosis. By testing the RT-LAMP against ZIKV, non-specific amplification was screened when high concentrations of DNA was present. Lau et al. (2015) reported their screening test (Table 3 below) and found that assay to be highly specific to DENV RNA. Given the increased concentration of primers in the RT-LAMP assay reaction mix, the potential for that increased in non-specific amplification was tested. Most of the data in Table 3 was reported from Lau et. al, which uses the same set of primers as the disclosed RT-LAMP. The assay was tested against Dengue virus-1-4 (DENV1-4), JEV, CHIKV, and SINV. All dengue positive samples showed positive results while other viruses (in patient samples) were all negative. The disclosed RT-LAMP assay also showed specificity for DENV against ZIKV. From the results against ZIKV, the optimized reaction mix did not affect the selectivity of the RT-LAMP assay.

TABLE 3

Specificity data for DENV RT-LAMP assay.

| Type of Virus | Primer Reactivity |
|---|---|
| Dengue virus-1 (DENV-1) | + |
| Dengue virus-2 (DENV-2) | + |
| Dengue virus-3 (DENV-3) | + |
| Dengue virus-4 (DENV-4) | + |
| Japanese Encephalitis virus (JEV) | − |
| Chikungunya virus (CHIKV) | − |
| Sindbis virus (SINV) | − |
| Zika virus (ZIKV) | − |

Figure 7A:
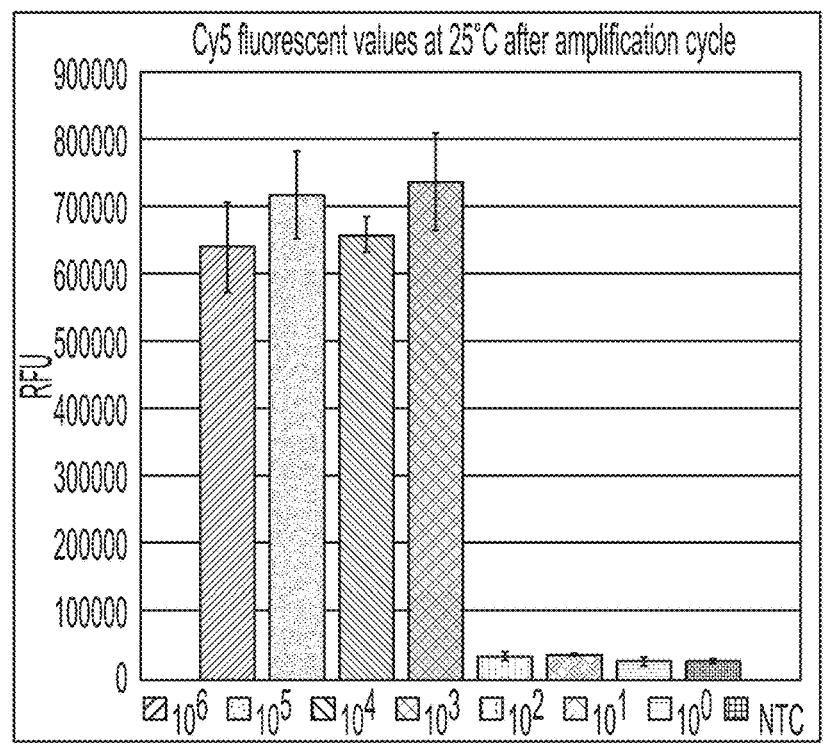

The Cy5 fluorescent intensity is a direct measure of the amount of target amplicons present in each tube at the end of the reaction due to their incorporation of labelled primers. Higher input RNA concentrations would be expected to lead to higher Cy5 fluorescent values. However, the highest fluorescent Cy5 intensities was observed in the lowest detected RNA concentration of $10^3$ copies per reaction (FIG. 7A). There is no particular trend in the mean Cy5 fluorescent values as the input RNA concentrations were varied from high to low. This suggests that kinetics of the reduced volume LAMP reaction vary from a traditional LAMP assay where either a linear standard curve or a log-linear standard curve were achieved.

Figure 7B:
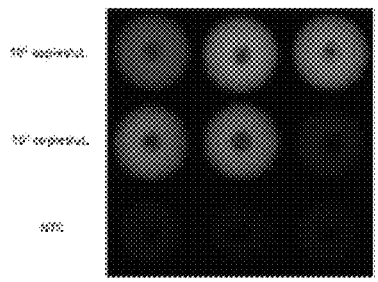
Figure 7C:
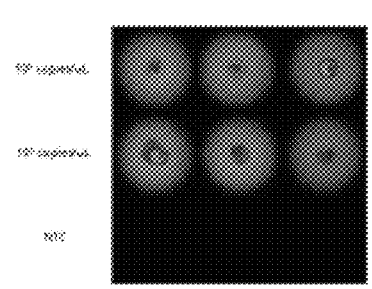
Figure 7D:
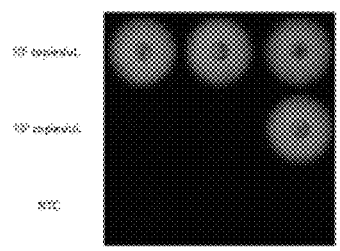

The RT-LAMP assay was tested for viral infections Influenza A, Influenza B, Rhinovirus, and SARS Co-2 (Orf1 and N). LAMP assay was carried out with samples of $10^6$ copies/µL and $10^3$ copies/µL, a standard primer concentration, 1.6 µM FIP/BIP-Cy5, 0.2 µM F3/B3, 0.8 µM LF/LB (0.4 µM LF1 LF2 and 0.8 µM LB for Rhinovirus), 2.4 µM Quencher, 0.32 Units/µL Bst 2.0 WarmStart® Polymerase enzyme at 67° C. for 40 minutes. End point images were taken at 635 nm excitation at room temp. Bright Cy5 fluorescence spots were observed after amplification at the printed locations for both concentrations for Influenza A (FIG. 7B), Influenza B (FIG. 7C), and Rhinovirus (FIG. 7D). Amplification plot (FIG. 7E) and Ct value (FIG. 7F) show amplification at both RNA concentrations for all three viruses. Standard primer concentration, 1.6 µM FIP/BIP-Cy5, 0.2 µM F3/B3, 0.8 µM LF/LB (0.4 µM LF1 LF2 and 0.8 µM LB for Rhinovirus), 2.4 µM Quencher, 0.32 Units/µL Bst 2.0 WarmStart® Polymerase enzyme at 67° C. for 40 minutes. End point images were taken at 635 nm excitation at room temp. Fluorescence for SARS Co-2 Orf1 was similar to control (FIG. 7G), whereas bright fluorescent spots were observed after amplification for SARS Co-2 N (FIG. 7H).

Figure 7I:
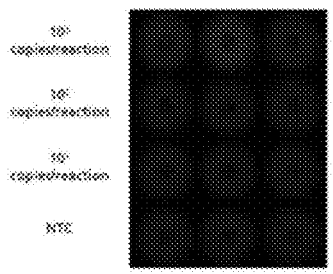
Figure 7J:
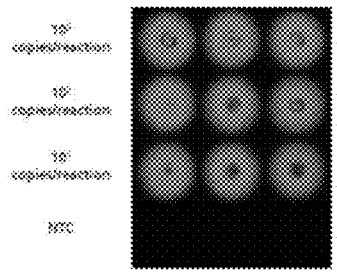
Figure 7K:
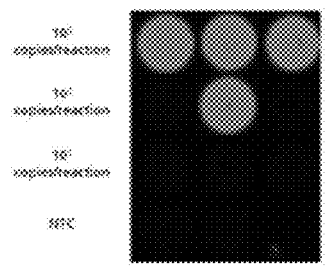
Figure 7L:
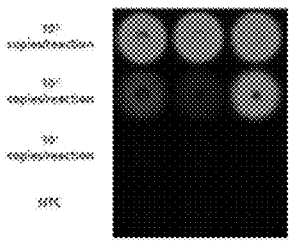

LAMP assay for each virus was tested at lower concentrations of sample for clinically reported lowest loads, at $10^1$ copies, $10^2$ copies, and $10^3$ copies each, with 4.8 µM FIP/BIP-Cy5, 0.2 µM F3/B3, 0.8 µM LF/LB, 7.2 µM Quencher, 0.64 Units/pL Bst 2.0 WarmStart® Polymerase enzyme at 67° C. for 40 minutes. End point images were taken at 635 nm excitation at room temp. Influenza A was not detected at any level (FIG. 7I), Influenza B was positive for all concentrations (FIG. 7J), and Rhinovirus (FIG. 7K) and SARS CoV-2 N (FIG. 7L) were positive for $10^2$ and $10^3$ copies.

TABLE 4

Lowest Limited of Detection for Viruses

| Copy number | Positive Amplification (replicates) HRVA | Positive Amplification (replicates) IBV |
|---|---|---|
| $10^5$ | 9/9 | 9/9 |
| $10^5$ | 9/9 | 9/9 |
| $10^4$ | 9/9 | 9/9 |
| $10^3$ | 8/9 | 9/9 |
| $10^2$ | 3/9 | 3/9 |
| 10 | 1/9 | 0/9 |
| 1 | 0/9 | 0/9 |
| No template | 0/9 | 0/9 |

Figure 7M:
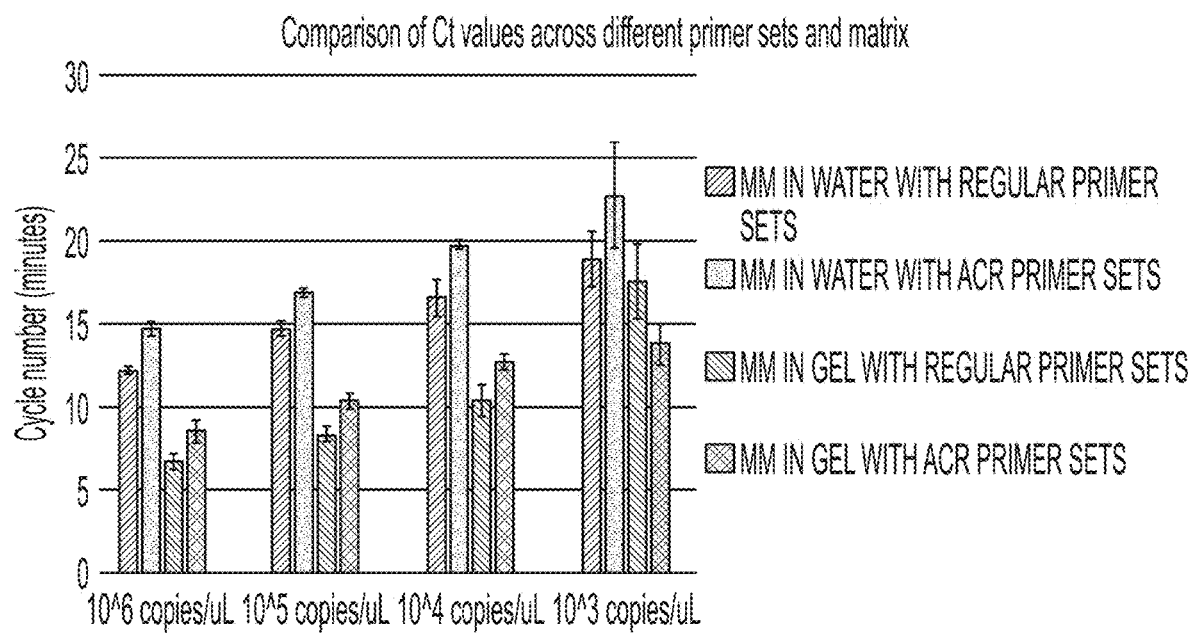

LAMP assay was tested in-tube in water and gelatin with acrydite primer sets, comparing three natural oligos and three acrydite oligos: FIP, Loop B, Loop F. Acrydite primers were covalently link to hydrogel under UV at varied concentration of RNA, $10^6$ copies/W, $10^5$ copies/µl, $10^4$ copies/W, and $10^3$ copies/W. Four groups were assayed: master mix in water with regular primer sets; master mix in water with FIP crydite_BIPCy5, F3_B3, AcryditeLoop B_AcryditeLoopF; master mix in 10% wt GM2A8 with regular primer sets; and master mix in 10% wt GM2A8 with FIP acrydite_BIPCy5, F3_B3, AcryditeLoop B_AcryditeLoopF. Representative repetitions (n=3); results for $10^3$ copies/uL data for master mix in gel with ACR primer sets is n=2 as one replicate failed to amplify. Comparison of Ct values across the different primer sets and matrix showed increase across all groups for $10^3$ copies/W. (FIG. 7M).

Example 2

Hydrogel Based Nucleic Acid Amplification Assay

Hydrogels are polymeric materials which swell up in the presence of water and are able to hold a distinct three-dimensional shape. They were among the first biomaterials developed for human use (Kopecek, et al., 2007) and have widely been used in various tissue engineering applications. They are promising biomaterials for the detection of various biomolecules including RNAs, because of their biocompatibility and the ease of adding various physical and (bio) chemical functionalities (Choi, et al. 2018). Hydrogels have also been used as a long term storage matrix for PCR reagents and as a filter to identify pathogens in whole blood (Beyer, et al. 2016). Based on the in situ polyacrylamide based PCR (Mitra et al., 1999), integrating hydrogel with the nucleic acid amplification reaction would (a) help store reagents on chip by mixing them in a gel, (b) restrict diffusion of viral DNA/RNA across the crosslinked gel which in turn could increase sensitivity of the hydrogel based assay. Also, hydrogels are suitable for contact free, high throughput inkjet printing. Researchers have demonstrated production of DNA/protein microarrays using inkjet printing on non-porous substrates, such as glass and plastic (Mujawar, et al. 2014). Inkjet printing allows precise dispensing at picoliter volume in predefined locations, thus allowing large numbers of parallel amplification assays to be performed on a single chip, leading to more accurate detection.

Here, acrylated and methacrylated gelatin formulations were tested with inkjet printing for compatibility. $GM_{10}$ tested at various concentrations from 5% to 15% showed optimum results for a 10% (w/v) hydrogel.

The UV conditions required for crosslinking and attaching the hydrogel to a glass based substrate was further characterized and a stable hydrogel attachment was achieved for at least 12 hours. Also, LAMP reagents can be dried on top of crosslinked hydrogels and stored for a period of 30 days at 37° C. without losing enzyme activity (with the exception of reverse transcriptase). Reagent diffusion studies showed that lower molecular weight components such as primers and polymerases were free to diffuse across crosslinked gels while higher molecular weight DNA targets were localized along the hydrogel spot boundaries. By integrating the hydrogel in the RT-LAMP assay, the limit of detection was increased by 100 fold to 10 copies per reaction.

Hydrogel Ink and Piezoelectric Printing

Piezoelectric inkjet printing is an attractive non-contact technique and drop-on-demand method for creating microarrays on a variety of substrates (Jung, et al. 2018). The ink required for this application needs to be both printable and also incorporate hydrogel precursors, which help provide the ability to crosslink into stable hydrogels after printing. Thus, ink development requires adjusting solution properties such as viscosity and surface tension. For inkjet printing, the viscosity of the ink should be on the lower side typically between 1 mPa s and 10 mPa s (Hoch, et al. 2013) as the power generated by the piezoelectric dispenser can be limited.

Different formulations of the methacrylated $GM_{10}$ hydrogel with varying weight percentages and composition on the sciFLEXARRAYER s3 (Scienion AG, Germany) spotter (Table 5).

TABLE 5

Stability of the printing process of GM10 hydrogel ink formulations with varying mass fractions and viscosities.

| Hydrogel Ink Formation | Stable Printing |
|---|---|
| $GM_{10}$-5% (w/v) | Yes |
| $GM_{10}$-10% (w/v) | Yes |
| $GM_{10}$-15% (w/v) | No |
| $GM_{10}$-10% (w/v) in 50% (v/v) glycerol | No |
| $GM_{10}$-10% (w/v) in 50% (v/v) glycerol | No |

High weight percentages of all the modified gels (10-15% w/v) were either not printable or exhibited irregular drop formation. Glycerol made the ink too viscous for inkjet printing and was unable to result in a stable printing process. Including a further filtration and spinning down step during hydrogel provided consistent and reliable drop formation with most inks (Table 5). For consistent and reliable drop formation, the volume of drop should not change drastically (±20 pL) in between multiple dispensing runs (measured by Autodrop function in Scienion software) and across repetitions (n=3). As reported, the 5% (w/v) $GM_{10}$ and 10% (w/v) $GM_{10}$ hydrogel formulations both resulted in a stable printing process. The 15% (w/v) $GM_{10}$ did not print reliably without observing satellite drop formation in between runs or clogging the nozzle. From prior analysis of degree of swelling and mechanical strength data (Hoch, et al. 2013), it is known that higher mass fractions lead to an increase in mechanical strength and a decrease in degree of swelling. Here, a hydrogel ink with a lower swelling ratio (smaller mesh size) was attempted to facilitate entrapment of higher molecular weight LAMP amplicons while allowing diffusion of lower molecular weight LAMP components. For development of the amplification using $GM_{10}$, the 10% (w/v) hydrogel was chosen for hydrogel ink.

Figure 8A:
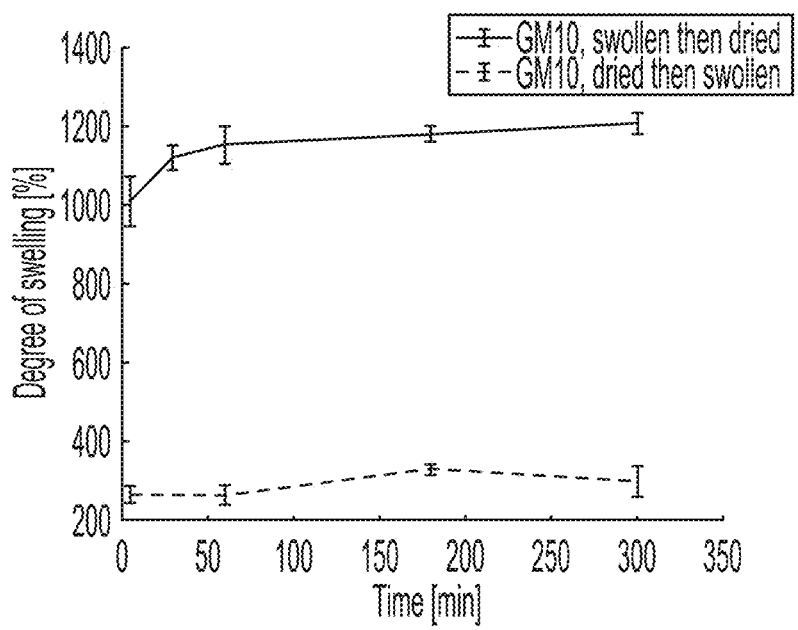
FIGS. 8A-8I illustrate properties of hydrogel drop formation.
Figure 8B:
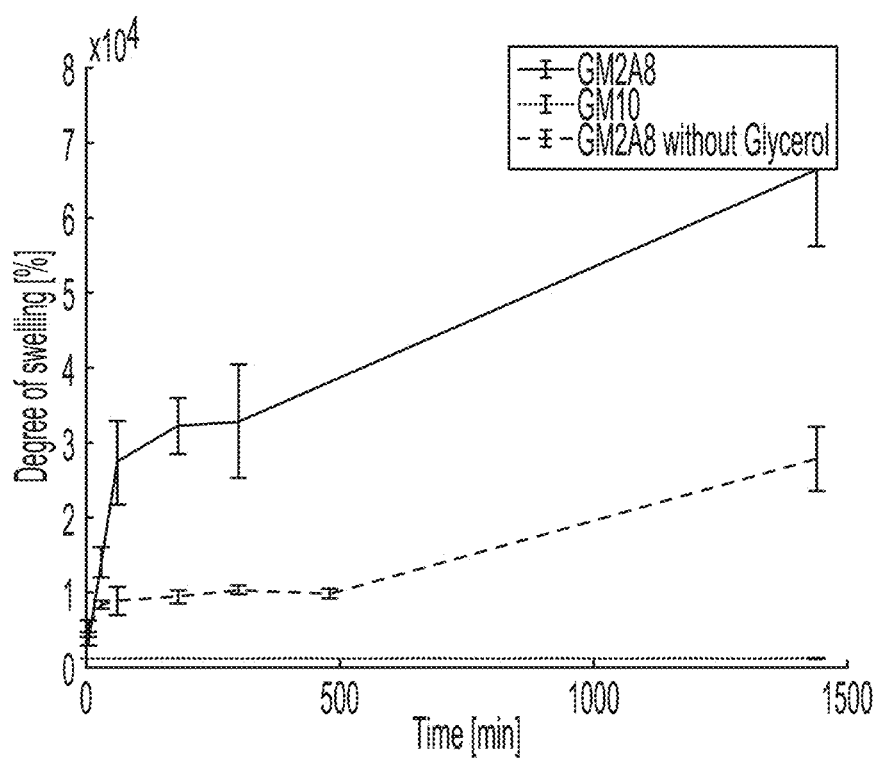

The hydrogel swelling ratio is important because it determines the final volume of the get compartment. Gel spots can detach if the swelling ratio is too great (expand and detach once liquid is added. Degree of swelling was tested for 10 wt % $GM_{10}$ and $GM_2A_8$ with 0.3 wt % LAP, 5 wt % Glycerol, crosslinking for 2 min at about 11 mW $cm^2$. Drying of hydrogels decreases swelling degree (FIGS. 8A-8B).

Figure 8C:
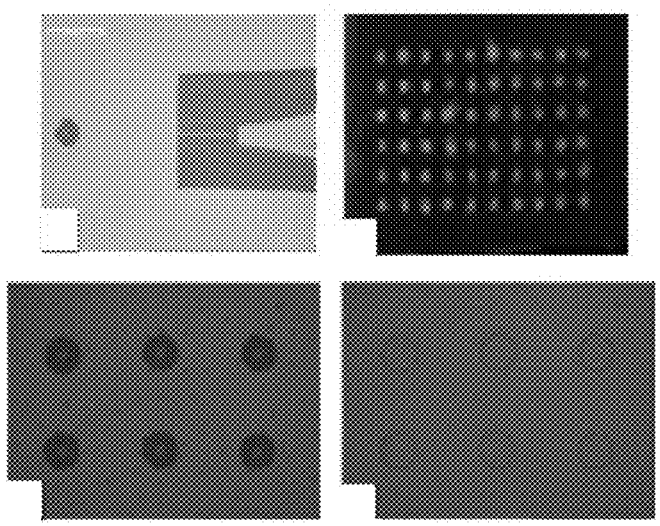

Along with facilitating entrapment of higher molecular weight RNA or DNA amplicons, and allowing diffusion of lower molecular weight molecules like ions, primers, and enzymes throughout the gel and not inhibit the assay, an ideal hydrogel should not interact with a sample RNA or DNA, and should hold it in place either electrostatically or due to size (mesh size of crosslinked gel smaller than size of virion), and should allow consistent, reliable printing (not clog up the nozzle). Another methylacrylated gelatin, $GM_2A_8$, reported to be slightly less viscous as compared to $GM_{10}$ (3.9+0.3 mPa s, 4.4+1 mPa s at 25° C.; Hoch et al. J. Mater. Chem. B, 2013) was investigated. $GM_2A_8$ was mixed with 5% glycerol (v/v) for a similar viscosity as a final probe with LAMP reaction mix (0.5% wt LAP with respect to gel). Two weight percentages, 5% and 10%, were tested for effect of strength and effective mesh size, as increase in molar weight of gelatin increases mechanical strength, but swelling capacity decreases (due to lower mesh size). Probes were used at temperature (22° C.) with a volume per drop targeted at 500 pL, and the number of drops at 100. (FIG. 8C).

LAMP assay made in $GM_2A_8$ matrix for a final 10% wt concentration. The reaction volume for printing was about 40 nL (80 drops per spot). LAMP master mix was printed first, and then sample (DNA/EB at about 10 nL) was printed on top of the previous spots. Reliable drop formation for LAMP master mix was attained for 10% wt $GM_2A_8$. Some irregular dispensing was eliminated with a short pre-run to check before the actual printing. Humidity was maintained in a closed chamber using moist cloth. If spots dry before or during the heating process, no fluorescence can be observed after amplification step (if there is one).

Figure 8D:
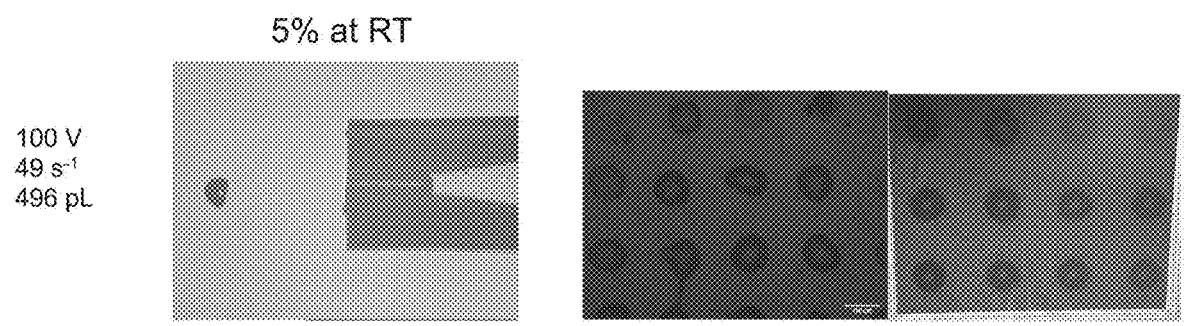
Figure 8E:
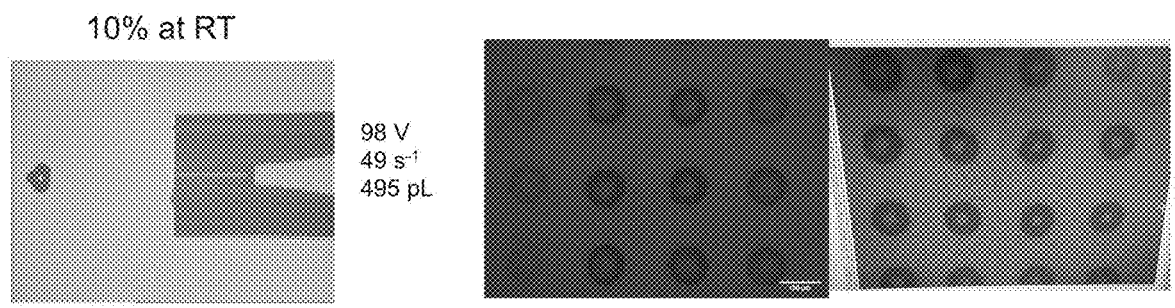
Figure 8F:
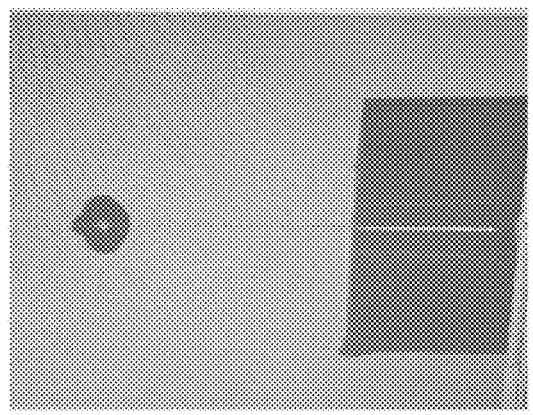

$GM_2A_8$ resulted in a stable printing process at 5% concentration in water (FIG. 8D) and 10% concentration in water (FIG. 8E), with 10% showing higher stability. $GM_2A_8$ also resulted in a stable printing process with 10% in gelatin. (FIG. 8F).

Using a one-step protocol (data not shown) in which hydrogel was mixed with LAMP reagents along with sample (~100 nL) and then printed, some issues with evaporation and ring fluorescence were observed, as with $GM_{10}$.

Figure 8G:
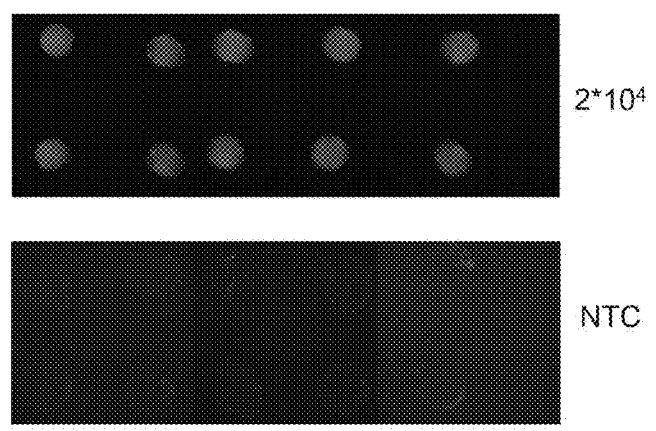
Figure 8H:
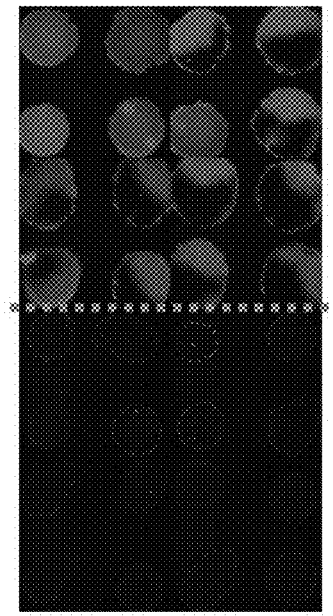

In a two-step protocol, hydrogel at about 25 nL was printed on glass substrate and crosslinked, LAMP reagents along with sample $2\times10^4$ copies per reaction, at about 100 nL was then printed on top of the hydrogel spots. (FIG. 8G). In another test, hydrogel at about 100 nL was printed and cross linked, and 100 nL LAMP with sample mix layered on the hydrogel (FIG. 8H). For both assays, UV crosslinking for 3 min at 8-9 $mW/cm^2$, 67° C. for 15 min, images at 635 nm. The lower hydrogel volume has a more defined printed spot and cleaner fluorescent intensity, which may be a factor of swelling ratio of hydrogel.

Figure 8I:
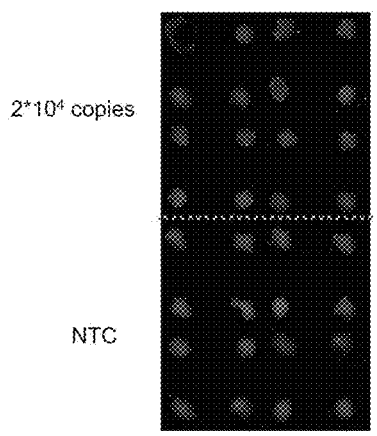

A three-step protocol was also tested, with hydrogel at about 100 nL printed on glass substrate and crosslinked, and then LAMP reagent master mix at about 80 nL was printed on top of the hydrogel spots. Then, a sample at about 20 nL was printed on top of the same spots to simulate a field lab setting where the chip would have all the assay components printed prior to introducing the sample. UV crosslinking step was run for 3 min at 8-9 $mW/cm^2$. Slides were enclosed in petri dish wrapped with parafilm and put on hotplate at 67° C. for 15 mins for the amplification step; imaged at 635 nm excitation. It was observed that fluorescence can be washed away by rinsing a glass slide with water, even though the hydrogel spot swelling can be observed. Since fluorescence can be washed, this indicates amplicons were smaller than mesh size of crosslinked gel. (FIG. 8I). These and other tests show that reagent components can be trapped by the hydrogels using small sample volumes, covalently linking primers to the material, such as acrydite primers (retain amplicons), as well as positively charged $GM_2A_8$ that can electrostatically attract the highly negative nucleic acids and dNTPs (from the phosphate groups).

Hydrogel Crosslinking and Attachment to Device Substrate

The UV parameters required for crosslinking and attaching to the device were established. For these experiments, both glass slides and cyclo-olefin polymer (COP) sheets were used as the device substrate. To facilitate adhesion of the hydrogel to a surface, the substrate was treated with TMSPMA, which creates a silanized layer. The settings that use the lowest power intensity and take the shortest time to crosslink would be considered as the optimal UV parameters. This was done to eliminate the need of specialized high powered UV sources. From Table 6, presents ideal attachment for a number of different settings. Based on the criteria mentioned above, a UV intensity of 9 mW cm-2 for 2 minutes was chosen for final parameters.

TABLE 6

UV parameters for $GM_{10}$ hydrogel crosslinking and attachment to device substrate

| UV parameters | Number of adhesion spots remaining after |
|---|---|
| 9 mW $cm^{-2}$ for 10 s | 0/3 |
| 9 mW $cm^{-2}$ for 30 s | 0/3 |
| 9 mW $cm^{-2}$ for 2 min | 3/3 |
| 39 mW $cm^{-2}$ for 10 s | 0/3 |
| 39 mW $cm^{-2}$ for 30 s | 3/3 |

Diffusion of LAMP Reagents within Hydrogel Matrix

Hydrogel characteristics are important features for small volume assay control. Ideally, a hydrogel matrix should allow free diffusion of small molecules with molecular weight such as water, ions, primers (<50 bp, MW<15.5 kDa), and enzymes (Bst 2.0 WarmStart® Polymerase: 97 kDa, WarmStart® RTx Reverse Transcriptase: 71 kDa), but restrict the diffusion of heavier DNA or RNA templates (>451 kDa) and subsequent amplification concatemers.

| Molecular weight guide for RT-LAMP reagents | |
|---|---|
| REAGENT | MOLECULAR WEIGHT |
| Water, ions, primers, dNTPs | <50 bp, MW < 15.5 kDa |
| Enzymes | 97 kDa, |
| Bst 2.0 Warm Start ® Polymerase | 71 kDa |
| WarmStart ® RTx Reverse Transcriptase | |
| DNA/RNA templates | >451 kDa |
| Fluorescein | 332 Da |
| Fluorescent beads | 40 nm |
| FITC BSA | 66 kDa |

Figure 9A:
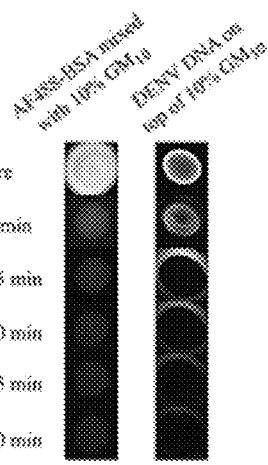
FIGS. 9A-9L: Diffusion within the hydrogel matrix.
Figure 9B:
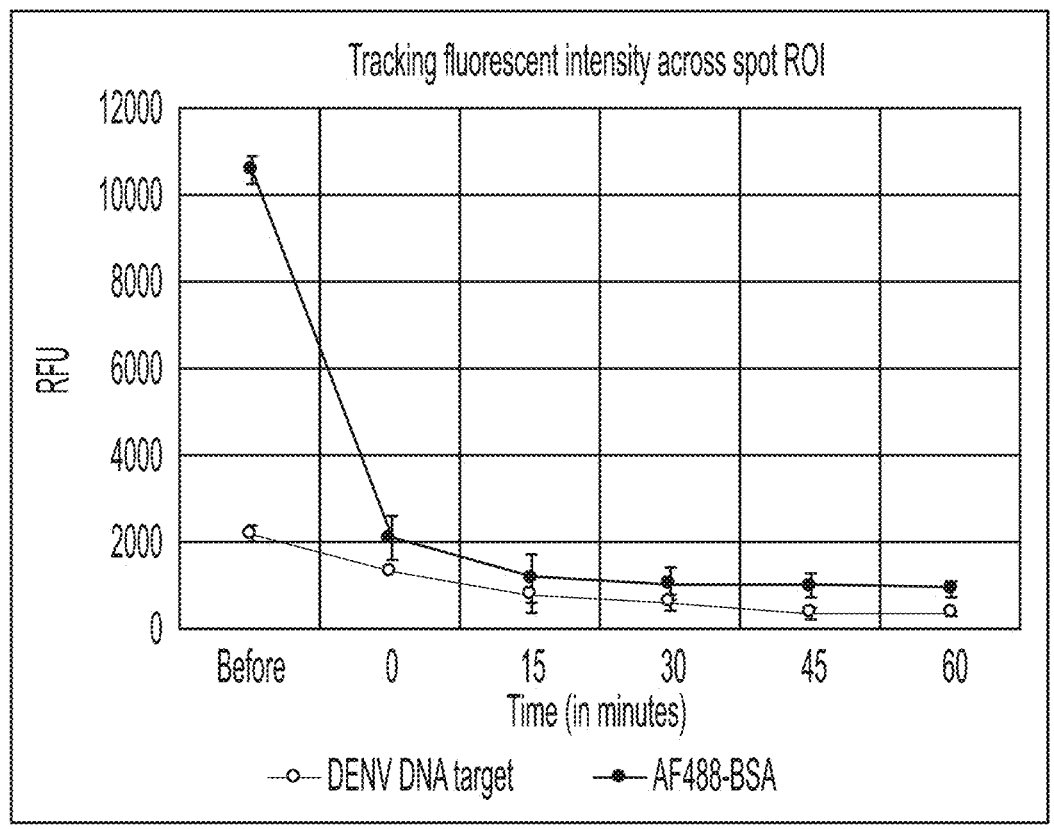

To verify that all LAMP reagents were free to diffuse within the UV crosslinked hydrogel, fluorescein and fluorescently tagged BSA (MW=67 kDa) were used to model the behavior of polymerase and reverse transcriptase enzymes as their molecular weights are close. Fluorescein models diffusion of ions primers and BSA models diffusion of enzymes. AF488-BSA mixed with 10% GM10 and DENV DNA layered on 10% GM10 diffusion were tracked, showing the diffusion of BSA was very fast in bulk solution (at 65° C.) as the spots were submerged in isothermal amplification buffer, while it was very nominal for the DNA target (FIG. 9A-9B). The apparent loss of fluorescence implies that BSA is diffusing into the solution from within the gel while fluorescent rings of DNA target around the hydrogel spots. (FIG. 9A). The mesh size of crosslinked hydrogels should allow free diffusion of RT-LAMP reagents and not cause any steric inhibition to the RT-LAMP assay while also collecting DNA around its surface.

To track how pore size (by regulating wt % of hydrogel) can affect diffusion rates of LAMP reagents, and whether hydrogel captures larger molecules like sample DNA or RNA at the surface or whether they are free to flow through, diffusion experiments with $GM_2A_8$ hydrogel were run using fluorescence recovery after photobleaching (FRAP), and using capillary tube tracking the diffusion of fluorescent proteins of varying molecular weights along the axial direction of the capillary tubes (Hettiaratchi et al., APL Bioeng., 2018; 2:026110).

Figure 9C:
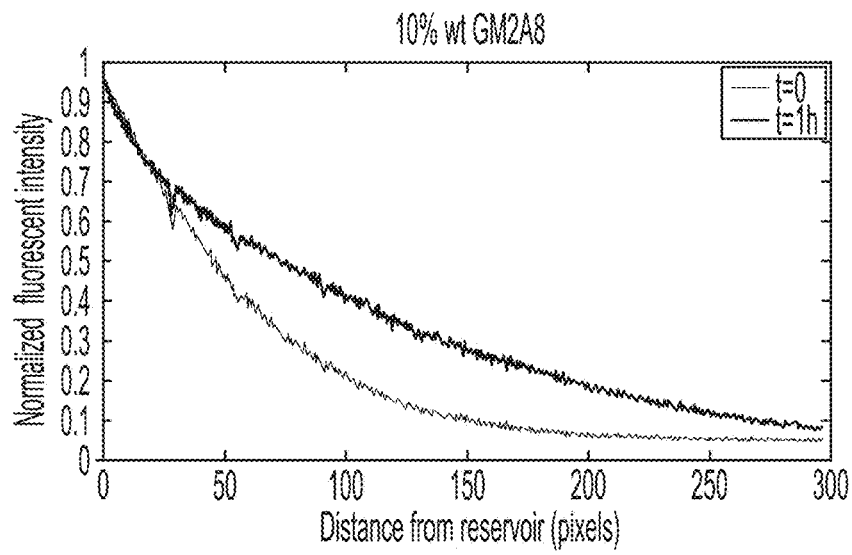
Figure 9D:
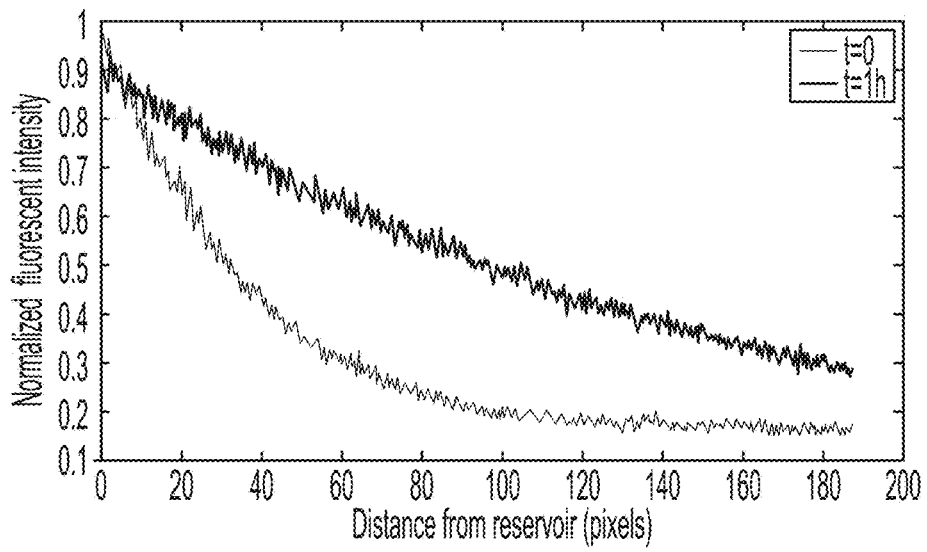
Figure 9E:
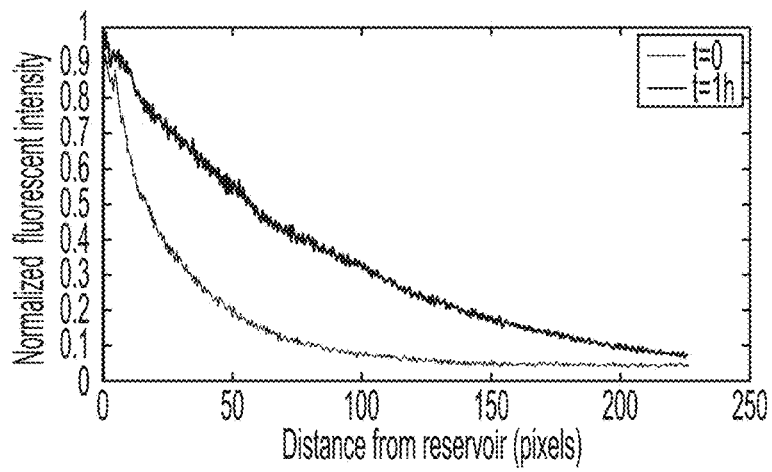
Figure 9F:
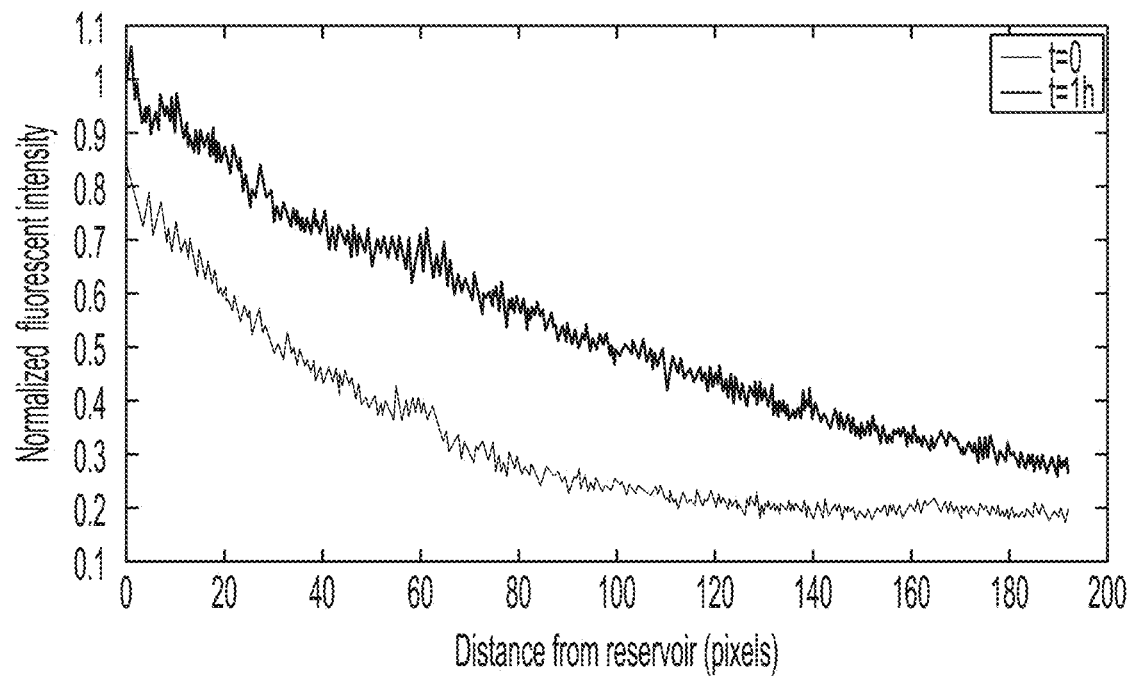

FRAP diffusion was run using fluorescein in PBS, and in $GM_2A_8$ hydrogel with 100 ul of 10% $GM_2A_8$ in 5% glycerol added to the center and crosslinked. The dishes were then filled with 100 uM fluorescein and five pre-bleach images captured. 4× lens was used to bleach the ROI with field stop closed and was then opened to capture FRAP time lapse. FRAP diffusion with fluorescein in PBS (FIG. 9C), Gaussian fit parameters Tau (frames) 39.226) had slightly faster diffusion from fluorescein in gel (FIG. 9D, Gaussian fit parameters Tau (frames) 109.282). Diffusion with FITC BSA in PBS, and in $GM_2A_8$ hydrogel using 100 ul of 10% $GM_2A_8$ in 5% glycerol was much slower. Dishes were filled with 10 ug/ml FITC BSA and 5 pre bleach images captured. 4× lens was used to bleach the ROI with field stop closed and was then opened to capture FRAP time lapse. Diffusion in FITC BSA in PBS (FIG. 9E, Gaussian fit parameters Tau (frames) 85.625), was still distinct from FITC BSA in hydrogel (FIG. 9F, Gaussian fit parameters Tau (frames) 139.475).

Axelrod's equation assumes unrestricted 2-D diffusion into a circular bleached area without recovery from above and below the focal plane, so it is valid only for diffusion in membranes. The equations mentioned above are derived using Ficks second law of diffusion and give a very rough approximation for the diffusion constants.

| Molecule | Diffusion constant ($\mu m2s \cdot 1$) |
|---|---|
| Fluorescein in PBS | 555.822 |
| Fluorescein in 10% wt GM2A8 | 194.855 |
| FITC-BSA in PBS | 40.502 |
| FITC-BSA in 10% wt GM2A8 | 25.453 |

Figure 9G:
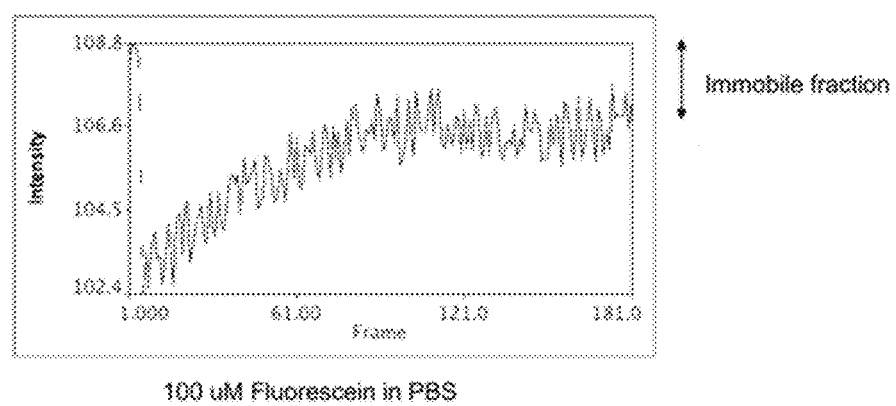
Figure 9H:
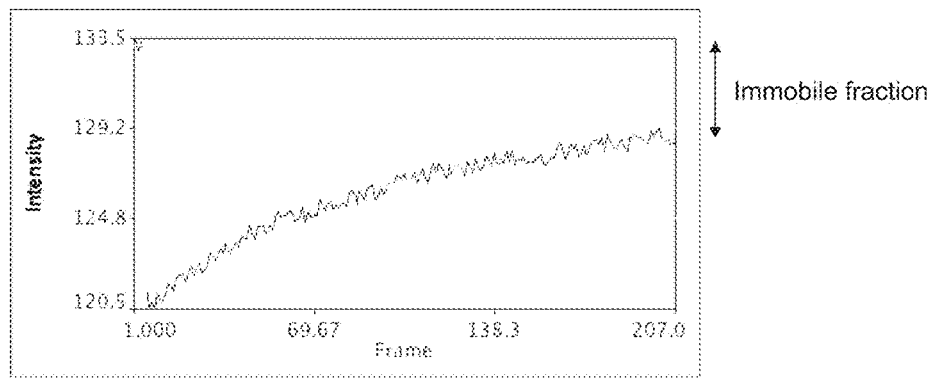
Figure 9I:
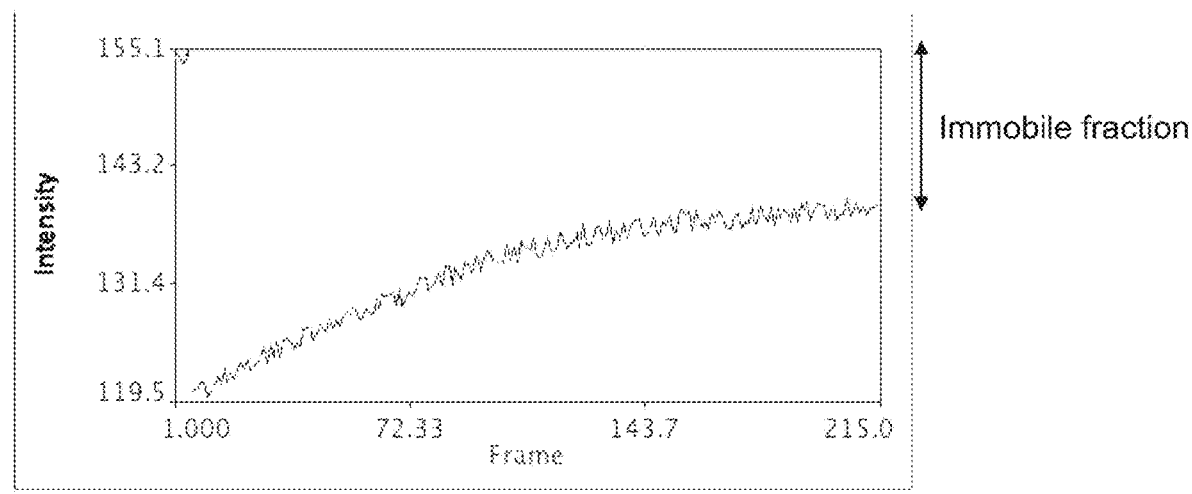
Figure 9J:
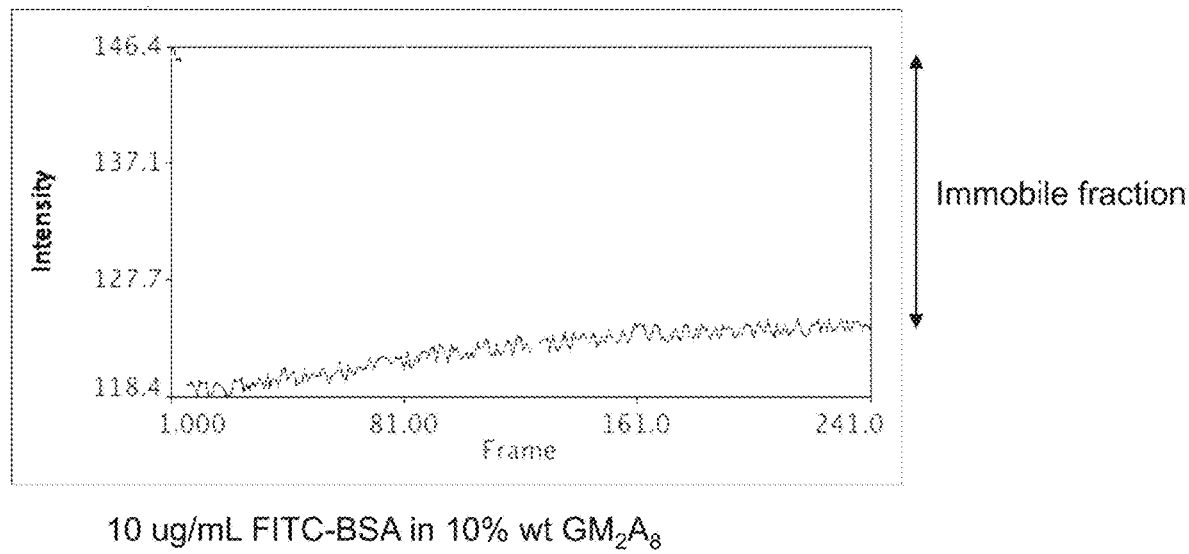
Figure 9K:
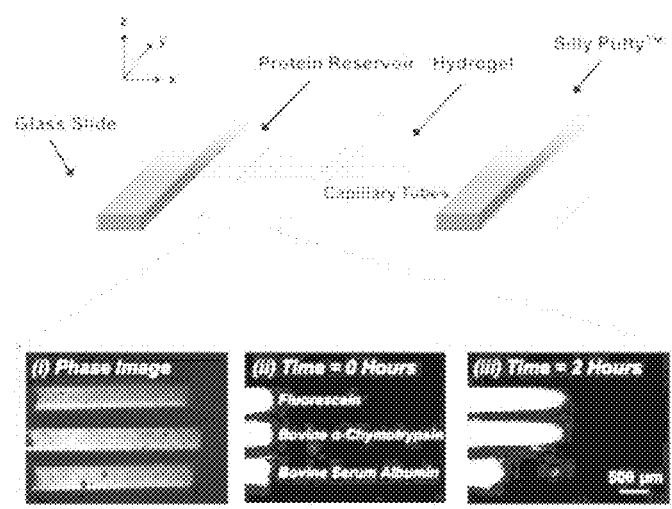
Figure 9L:
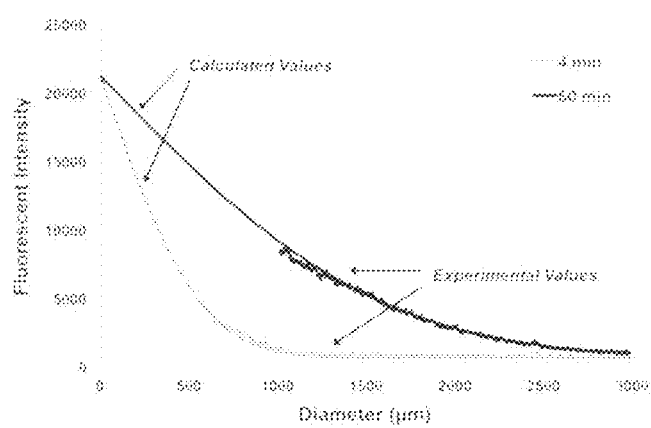

However, the diffusion parameters are strongly dependent on experimental parameters such as the radius of the user-defined bleach spot and the exact curve fitting protocol and this often leads to variations in theoretically derived parameters and experimental measure parameters. Capillary tube diffusion is another estimation model that can also provide an estimation of experimental measure parameters from calculated parameters. (FIGS. 9G-9H).

Substrate

Figure 10A:
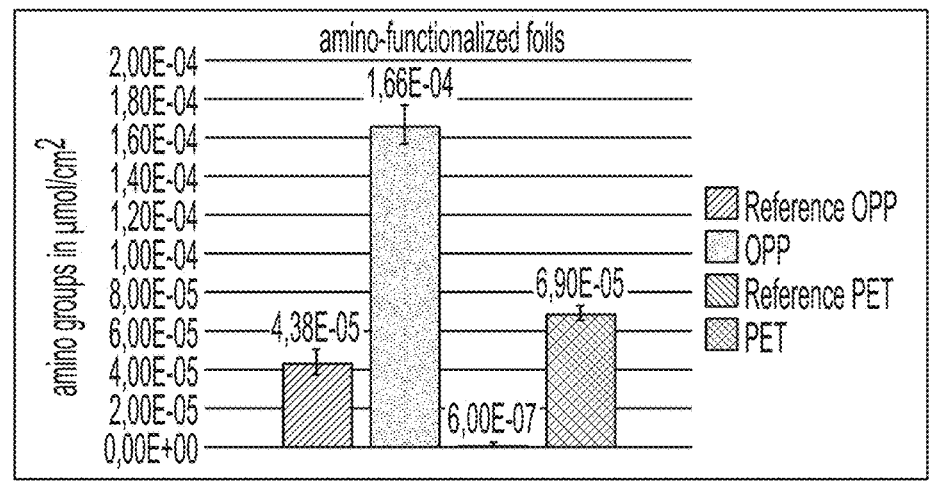
FIGS. 10A-10O: Adherence and contact angle for substrates. Functionalized OPP and PET foil films assessed using a sulfosuccinimidyl-4-o-(4,4-dimethoxytrityl) butyrate (Sulfo-SDTB) assay for amino groups on the surface. Both foils showed more amino groups than their references (FIG. 10A). Within 7 days, the amino groups on the foils were stable (FIG. 10B). Time dependent measurements show stable contact angle for functionalized OPP and PET foils for about 7 days, with OPP having a higher contact angle than PET (FIG. 10C). This difference is also evident in methacrylation of amino functionalization of the polymer foils OPP (FIG. 10D) and PET (FIG. 10E). Contact angle for $GM_{10}$ in water on TMSPMA polymer coated glass, and methacrylated OPP and PET evident after five days.
Figure 10B:
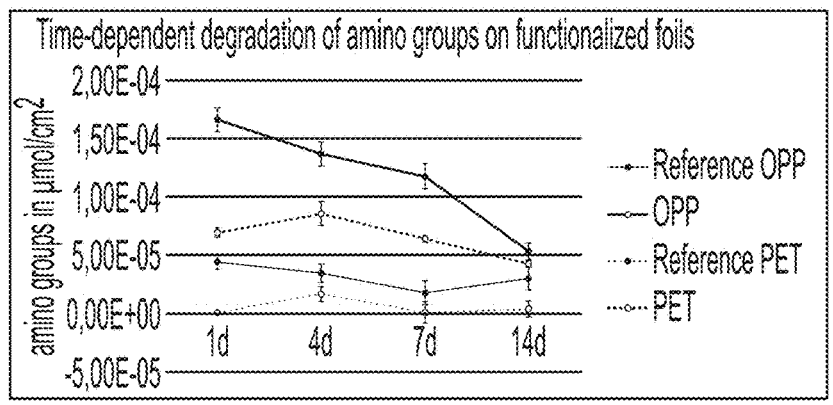
(FIG. 10F). Adherence test for PET at room temperature showing amino functionalized and methacrylated PET after crosslinking (FIG. 10G), and after 48 hours in water and 1 minute ultrasonic bath (FIG. 10H), compared to untreated (FIG. 10I) and untreated after 48 hours (FIG. 10J). Similar results are found with wet-etched 12% filter paper silanized with TMOS.
(FIG. 10K). Temperature at 62° C. does not influence spot adherence.
(FIG. 10L). Adherence test on PET and OPP after drying of plastic foils for one week, then placed foils in water for performed adherence test.
(FIG. 10M) Adherence test on Supor-100 PES Membrane after 24 hours in water, amino functionalized and methacrylated versus nonfunctionalized (FIG. 10N). Both unfunctionalized and methacrylated PES retained 100% adherence of hydrogel to the PES membrane at room temperature (about 22° C.) and at 62° C.; n=3.

Various substrates may be used in the biogel nanosensor, including glass, polymer films, paper forms such as filter paper, silanized paper, or hydrophobic paper, and plastic such as oriented polypropylene (OPP), polyethylene terephthalate (PET), polyether sulfone (PES), or polydimethylsiloxane (PDMS), all of which may be coated or functionalized. Complex microfluidic design needed for glass and plastic is not required with paper that allows direct application of sample to the spots. Functionalized OPP, PET, and PES films were assessed using a sulfosuccinimidyl-4-o-(4, 4-dimethoxytrityl) butyrate (Sulfo-SDTB) assay for amino groups on the surface. Both OPP and PET foils showed more amino groups than their references (FIG. 10A). Within 7 days, the amino groups on the foils were stable (FIG. 10B).

Hydrophilic amino groups were also detected via contact angle measurements. For PET the static contact angle of the functionalized foils decreased from 73° to about 40°. For OPP the static contact angle of the functionalized foil decreased from 91° to about 84°.

| Sample | OPP | PET |
|---|---|---|
| Reference | 91.0° ± 0.95° | 73.4° ± 2.5° |
| Functionalized foil after 1 day | 85.3° ± 1.6° | 36.8° ± 0.8° |
| Functionalized foil after 7 days | 84.4° ± 1.3° | 39.5° ± 0.3° |
| Functionalized foil after 14 days | 80.5° ± 0.6° | 40.5° ± 0.3° |

Figure 10C:
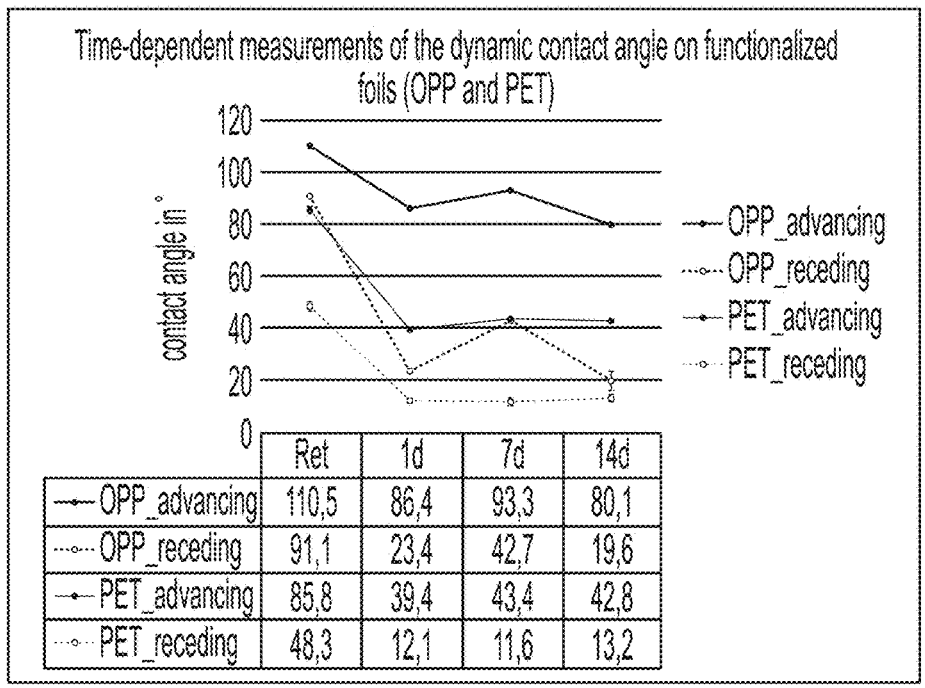
Figure 10D:
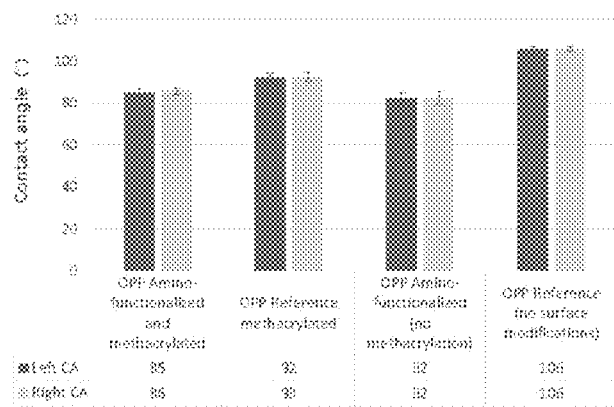
Figure 10E:
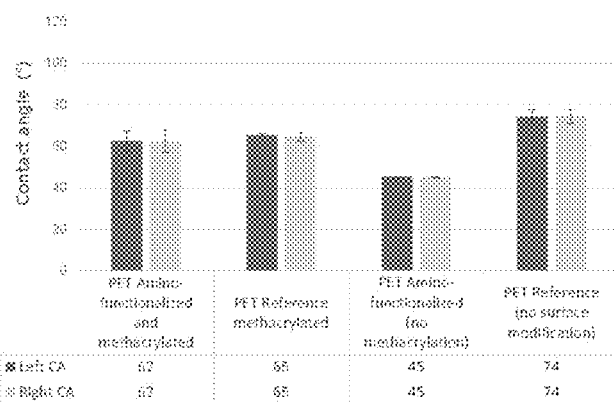

Advancing contact angle is observed with wetting of the foil, and receding contact angle is observed with drying of the foil. Time dependent measurements show stable contact angle for all functionalized foils for about 7 days, with OPP having a higher contact angle than PET (FIG. 10C). This difference is also evident in methacrylation of amino functionalization of the polymer foils OPP (FIG. 10D) and PET (FIG. 10E), however contact angle measurements for amino functionalized and methacrylated PET was higher than amino functionalized alone. (FIG. 10E). A short-term stability test showed binding of GM10 in water on TMSPMA polymer coated glass, and methacrylated OPP and PET evident after five days. (FIG. 10F).

Adherence was tested for amino functionalized and methacrylated PET and OPP at room temperature, 4×4 hydrogel spots on each substrate, crosslinking for 2 minutes at 11.3 mW/cm$^2$ under argon (~100% rh), sample placed in cups with each 60 mL water on a shaker. Samples were examined until 48 hours in water, wash, and then one minute in a ultrasonic bath. Amino functionalized and methacrylated PET retained at crosslinking (FIG. 10G), and after 48 hours in water and one minute ultrasonic bath (FIG. 10H), compared to untreated (FIG. 10I) and untreated after 48 hours (FIG. 10J). Similar results are found with wet-etched 12% filter paper silanized with TMOS. (FIG. 10K). Adherence tests on PET and OPP after drying of plastic foils for one week, then the foils were placed in water for adherence testing. (FIG. 10M).

Figure 10O:
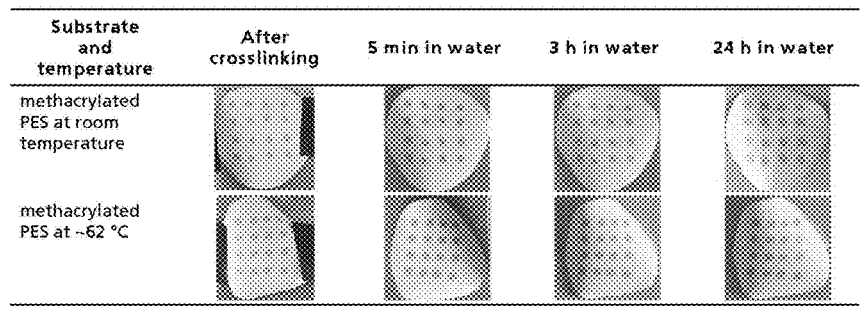

Polyether sulfone (PES) was also a strong substrate, with a high number of amino groups on the surface on functionalized PES membrane. Adherence tests for Supor-100 PES membrane for 24 hours in water, unfunctionalized and amino functionalized and methacrylated PES had strong adherence (FIG. 10N). Both unfunctionalized and methacrylated PES retained 100% adherence of hydrogel to the PES membrane at room temperature (about 22° C.) and at 62° C. (FIG. 10O)

Using paper membranes in device instead of glass/COP polyether sulfone (PES) and polycarbonate (PC) membranes may also act both as capture membranes for extracting RNA from clinical samples and be compatible and not inhibit isothermal amplification. (Rodriguez N M, et al. Anal Chem. 2015; 87(15):7872-7879; Linnes J C, et al. Biomed Microdevices. 2016 April; 18(2). Sl 17).

Paper membranes may be used in the biosensor device instead of glass or COP. Spotted paper membrane may be arrayed with reaction spots similar to glass or plastic, and packaged with a film/tape. The paper membrane would be wetted with amplification buffer to rehydrate reaction spots.

Limit of Detection of Gel Based DENV RT-LAMP Assay

Whether the hydrogel could itself inhibit the RT-LAMP reaction The previously optimized RT-LAMP assay in a tube was modified to replace water with GM10 hydrogel, such that the final weight percentage of $GM_{10}$ was 10% in the reaction. Corresponding Cy5 fluorescence was observed in tubes containing the DENV RNA target. A limit of detection study was also performed to test the integration efficiency of 10% $GM_{10}$. The lowest DENV RNA concentration that amplified in 100% of trials (n=6) was considered the assays limit of detection in a hydrogel matrix.

Figure 11:
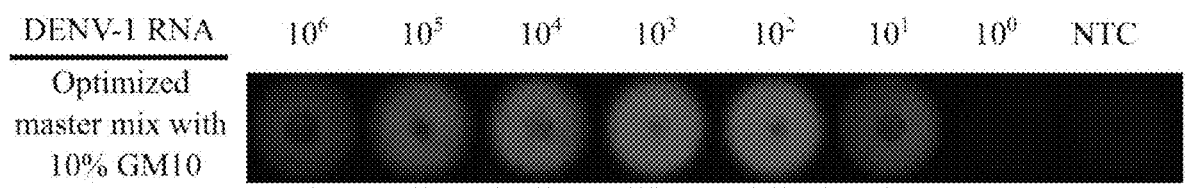
FIG. 11: Shows the limit of detection of DENV RT-LAMP assay.

When the RT-LAMP assay was transferred into a hydrogel matrix, the limit of detection was increased 100 fold to 10 copies per reaction (FIG. 11). This limit was well below clinically reported DENV RNA loads in serum (Gurukumar, et al. 2009) and is very close to the sensitivity of highly optimized LAMP reactions reported in literature. This may be due to restricted diffusion of large molecular weight LAMP concatemers within the hydrogel that increases its interaction.

Storage of LAMP Reagents in Hydrogel Matrix

Figure 12:
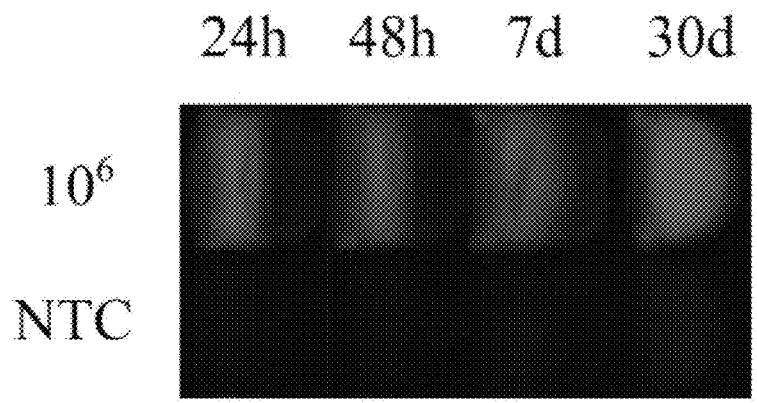
FIG. 12: LAMP reagents dried onto 10% (w/v) $GM_{10}$ hydrogels for long term storage at 37° C. The LAMP reaction mix containing only dNTPs, primers, dyes and polymerase was added on top of crosslinked gels, dried under laminar airflow and stored in sterilized packets at 37° C. The panel above shows Cy5 fluorescence readout of target amplicons at endpoint.

The stability of LAMP reagents such as polymerase, primers, dNTPs and reverse transcriptase when stored in 10% (w/v) $GM_{10}$ hydrogel was investigated. These LAMP reagents are usually stored at −20° C. for preserving their efficiency and this necessitates a cold chain requirement for any field deployment of a diagnostic LAMP assay. It has previously been shown that Bst 2.0 polymerase is relatively stable at 37° C. for a period of 30 days (Thekisoe, et al. 2008). The ability to preserve the reagents by drying them on top of UV crosslinked hydrogels was investigated. LAMP reactions that were previously air dried on crosslinked hydrogel by adding the template and buffers to make up the volume were reconstituted. Positive amplification of the DENV-1 DNA target (FIG. 12) was successfully determined for a duration of at least 30 days (n=3).

Example 3

Inkjet Printed Platform for Hydrogel Based RT-Lamp Assay

After validating the hydrogel based DENV RT-LAMP assay in vitro, the assay was adapted to an inkjet printed platform. The inkjet printing properties of the chosen hydrogel formulation (10% w/v GM10) and its adhesion to a glass or COP substrate was characterized above. The precise nature of piezoelectric inkjet printing was used to spot a microarray of hydrogel based DENV RT-LAMP reactions. This allows (a) reducing the volume of RT-LAMP reaction to nanoliters, which helps reduce the cost of reagents and number of amplification cycles required for positive detection (Dahl, et al. 2007), (b) approaching a digitized readout because of discretization of reactions and template, and (c) allowing multiplex detection on the same device by printing microarrays of RT-LAMP reaction containing respective primer sets alongside each other. These elements were used to validate the device. Further studies investigated (a) if the reduced volume (100 nL) hydrogel based DENV RT-LAMP assay would result in detectable Cy5 fluorescence intensities at the end of amplification cycle, (b) how to deliver sample to the printed RT-LAMP reaction spots, and (c) how to prevent evaporation of reaction and sample volume when the device was heated for the amplification cycle. Positive Cy5 fluorescence in printed hydrogel based RT-LAMP reactions was detected using a glass substrate when the template was premixed with the reaction. An increased rate of false positives observed in this setup was due to lack of aseptic RNA handling techniques. The reaction spots printed on glass substrate did not dry out during amplification when they were placed and sealed in a well plate. To manually deliver sample to printed RT-LAMP reaction spots, reservoirs (25 µL volume) were fabricated with drilled inlet and outlet ports using acrylic sheets and adhesive tape.

Manual delivery of samples to the hydrogel spots containing the LAMP reagents may be used with acrylic sheets used to create wells for manually pipetting hydrogel spots (5 µL) containing the LAMP reagents. Amplification via endpoint Cy5 fluorescence detection was demonstrated in manually pipetted spots containing the hydrogel based LAMP assay (DNA target was used instead to eliminate errors due to RNA contamination/degradation on device materials).

Array of Inkjet Printed Hydrogel Based Amplification Reactions

Figure 13:
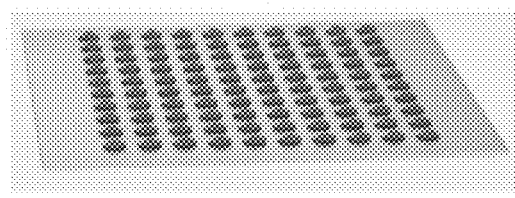
FIG. 13: Array of inkjet printed hydrogel based DENV RT-LAMP reactions. On the left is a graphical representation of 10% (w/v) $GM_{10}$ spots containing the DENV RT-LAMP (in pink) printed on a TMSPMA treated glass slide; on the right, positive Cy5 fluorescence readout of target amplicons at endpoint when $10^6$ copies of DENV RNA were added to the reaction mix.
Figure 13:
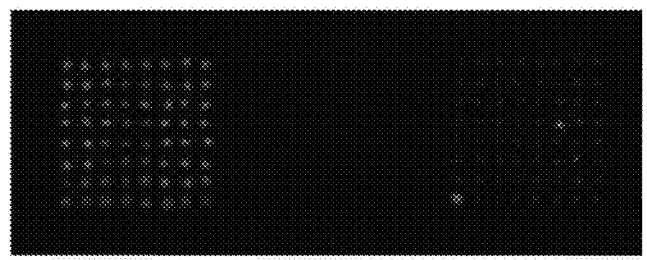

To adapt the hydrogel based DENV RT-LAMP assay to a 50 nL volume, an array (8×8) of 50 nL spots of 10% (w/v) $GM_{10}$ was printed on a TMSPA treated glass slide. After crosslinking these hydrogel spots, the DENV RT-LAMP reaction mix along with the corresponding template was printed on top of the hydrogel spots and dried in a humidified chamber for 30 minutes. Bright Cy5 fluorescence spots were observed after amplification at the printed locations indicating a positive readout (FIG. 13). One of the issues with this experiment was the high rate of false positives observed (in 2 out 4 cases) due to contamination.

Hydrogel Based NAAT on a Microarray Chip

Figure 14A:
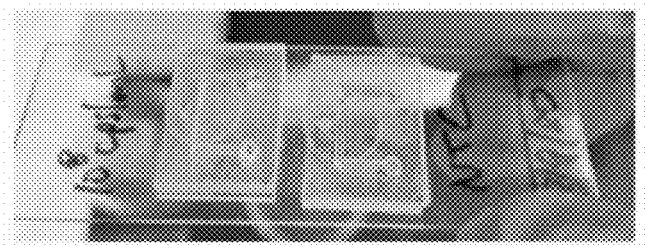
FIGS. 14A-C: Workflow for hydrogel based DENV LAMP assay without inkjet printing.
Figure 14B:
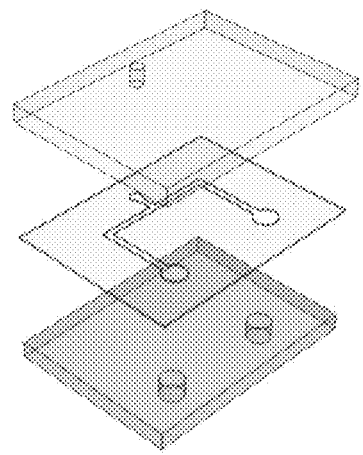
Figure 14C:
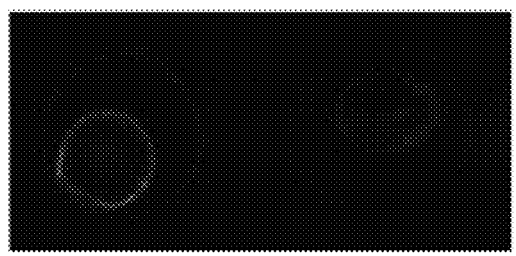

To develop the inkjet-printed device for nucleic acid amplification tests, laser cut acrylic sheets bonded to glass slides was used to create wells that were filled with 10% (w/v) hydrogel and crosslinked to the glass. As described in Example 2, LAMP reaction mix containing only the primers, dNTPs and polymerase were dried on top of these gels in laminar air flow. For ease of handling, two wells per device were used, but this could be easily increased by increasing the size of the device to incorporate more wells. Positive ($10^5$ copies/µL) samples resulted in target amplification in half the cases as confirmed by endpoint Cy5 fluorescence readout (FIG. 14). It is known that acrylic, glass and adhesive tape do not inhibit LAMP reactions themselves; the lower positive amplification rate appears to be handling techniques while assembling the device.

Figure 15:
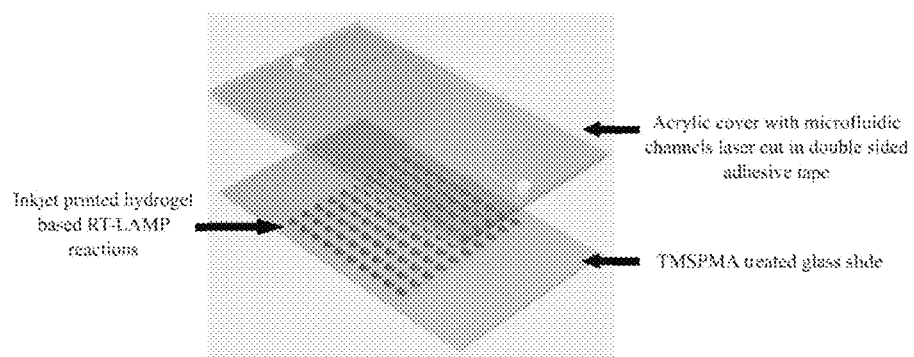
FIG. 15 illustrates an ink-jet printed hydrogel based DENV RT-LAMP assay device.

Platform Design for Inkjet Printed Hydrogel Based Nucleic Acid Amplification Assays Delivery of the sample to the printed hydrogel spots containing the RT-LAMP assay was a challenge to adapt the RT-LAMP assay to the new device format. As shown in Example 3, all LAMP reagents can freely diffuse from inside the cross-linked hydrogel into the bulk solution. Thus, a large sample volume would interact with the printed reactions, with a risk for diluting the assay components and making it very inefficient. Incorporating sample while printing the hydrogel reaction array was not unsuitable for in house clinical or POC testing. A microarray of 250 spots (50 nL reaction volume each) was printed and surrounded with a reservoir that can contain a volume of 25 µL. This ensured that the bulk solution volume would not dilute the concentration of the reagents, but instead act as a reservoir of 25 µL RT-LAMP reaction. Any DNA/RNA target present in the sample would get trapped around the printed hydrogel spots, resulting in bright fluorescent rings indicating target amplification. (FIG. 15).

Hydrogel formulations were validated as inkjet printing compatible. Reliable and precise printing of 10% (w/v) hydrogel in a range from 50 pL to 50 nL spots was shown using the precision dispensing system. Using fluorescently-labelled proteins of similar molecular weight as amplification reagents, free diffusion of the reagents within the crosslinked hydrogel was confirmed, while the heavier DENV DNA target localized around the hydrogel boundaries.

By incorporating the hydrogel to develop a gel based RT-LAMP assay (5 µL volume), the limit of detection was increased by 100 fold to 10 copies of DENV RNA per reaction. The assay is highly sensitive and suitable for diagnosis of early onset and asymptomatic viral infections. In a small time-scale study, the disclosed hydrogel based LAMP assay was stable for up to 30 days at 37° C., implying its suitability for on chip storage. Positive amplification of DENV RNA in inkjet printed gel based RT-LAMP assay in a range from 50 pL to 50 nL total volume was demonstrated.

A biogel nanosensor was developed that may use bioprinting of assay spots on a substrate such as glass, plastic, or polymer film, with or without translucent polymer coating, and laminated with biocompatible film. Alternatively, the substrate may be a porous material, such as paper, with bioprinting of assay spots directly on substrate. This alternative nanosensor may be biodegradable.

Detection Module

A portable reader would be used for detection of the amplification product. The reader could be a standalone device with a heating unit, an optical detection system (e.g. fluorescence), data acquisition capability, and preferably, a graphic user interface. The standalone reader may be compatible with a smartphone for some of those capabilities. Alternatively, a smartphone may be the reader device, which would have an analyzer capability or application.

Modules or elements of a reader or analyzer device may include a housing, a frame, a heating module, a detection unit (such as camera and fluorescence/colorimetric submodules), a control element (microcontroller or other device that can control the whole system). The reader may contain a display or may be connected to display module such as a smartphone.

The reader may accept the biogel nanosensor (POC test chip) directly. A cassette module may secure the nanosensor chip during operation.

REFERENCES

All references and publication cited in the specification and Examples are incorporated by reference herein in their entireties.

1. St John, A., and Price, C. P. (2014) Existing and Emerging Technologies for Point-of-Care Testing. *Clin Biochem Rev* 35, 155-167.
2. Pai, N. P., Vadnais, C., Denkinger, C., Engel, N., and Pai, M. (2012) Point-of-care testing for infectious diseases: diversity, complexity, and barriers in low and middle-income countries. *Plos Med* 9, e1001306.
3. Drain P K, Hyle E P, Noubary F, et al. (2014) Diagnostic point-of-care tests in resource limited settings. *Lancet Infect Dis.;* 14(3):239-249.
4. Brecher, C., Baum, C., and Bastuck, T. (2015) Comparison of roll-to-roll replication approaches for microfluidic and optical functions in lab-on-a-chip diagnostic devices. *Proc Spie* 9320.
5. Senkbeil, S., Aho, J., Yde, L., Lindvold, L. R., Stensborg, J. F., Rantanen, J., Lafleur, J. P., and Kutter, J. P. (2016) Roll-to-plate fabrication of microfluidic devices with rheology-modified thiol-ene resins. *J Micromech Microeng* 26.
6. Becker, H. (2009) It's the economy . . . *Lab Chip* 9, 2759-2762.
7. Land, K. J et al. (2019). In *Paper-based Diagnostics* (Springer International Publishing).
8. Hoch, E., Hirth, T., Tovar, G. E. M., & Borchers, K. (2013). Chemical tailoring of gelatin to adjust its chemical and physical properties for functional bioprinting. *Journal of Materials Chemistry B,* 1(41), 5675-5685.
9. Sanders, R., Huggett, J. F., Bushell, C. A., Cowen, S., Scott, D. J., & Foy, C. A. (2011). Evaluation of digital PCR for absolute DNA quantification. *Analytical Chemistry,* 83(17), 6474-6484.
10. Kolluri, N., Klapperich, C. M., & Cabodi, M. (2017). Towards lab-on-a-chip diagnostics for malaria elimination. *Lab on a Chip,* Vol. 18, pp. 75-94.
11. Meagher, R. J., Priye, A., Light, Y. K., Huang, C., & Wang, E. (2018). Impact of primer dimers and self-amplifying hairpins on reverse transcription loop-mediated isothermal amplification detection of viral RNA. *Analyst,* 143(8), 1924-1933.
12. Bhatt S, Gething P W, Brady O J, Messina J P, Farlow A W, Moyes C L, Drake J M, Brownstein J S, Hoen A G, Sankoh O, Myers M F, George D B, Jaenisch T, Wint G R, Simmons C P, Scott T W, Farrar J J, Hay S I. 2013. The global distribution and burden of dengue. Nature 496: 504-507.
13. Lopez-Jimena, B., Bekaert, M., Bakheit, M., Frischmann, S., Patel, P., Simon-Loriere, E., Weidmann, M. (2018). Development and validation of four one-step real-time RT-LAMP assays for specific detection of each dengue virus serotype. *PLoS Neglected Tropical Diseases,* 12(5).
14. World Health Organization. 2009. Dengue: guidelines for diagnosis, treatment, prevention and control. World Health Organization, Geneva, Switzerland.
15. Notomi, T., Okayama, H., Masubuchi, H., Yonekawa, T., Watanabe, K., Amino, N., & Hase, T. (2000). Loop-mediated isothermal amplification of DNA. In *Nucleic Acids Research* (Vol. 28).
16. Ball, C. S., Light, Y. K., Koh, C. Y., Wheeler, S. S., Coffey, L. L., & Meagher, R. J. (2016). Quenching of Unincorporated Amplification Signal Reporters in Reverse-Transcription Loop-Mediated Isothermal Amplification Enabling Bright, Single-Step, Closed-Tube, and Multiplexed Detection of RNA Viruses. *Analytical Chemistry,* 88(7), 3562-3568.
17. Priye, A., Bird, S. W., Light, Y. K., Ball, C. S., Negrete, O. A., & Meagher, R. J. (2017). A smartphone-based diagnostic platform for rapid detection of Zika, chikungunya, and dengue viruses. *Scientific Reports,* 7.
18. Fu, E. (2014). Enabling robust quantitative readout in an equipment-free model of device development. *Analyst,* 139(19), 4750-4757.
19. Sanders, R., Huggett, J. F., Bushell, C. A., Cowen, S., Scott, D. J., & Foy, C. A. (2011). Evaluation of digital PCR for absolute DNA quantification. *Analytical Chemistry,* 83(17), 6474-6484.
20. Kreutz, J. E., Wang, J., Sheen, A. M., Thomspon, A. M., Staheli, J. P., Dyen, M. R., Chiu, D. T. (2019). Self-digitization chip for quantitative detection of human papillomavirus gene using digital LAMP. *Lab on a Chip,* 19(6), 1035-1040.
21. Hoch, E., Schuh, C., Hirth, T., Tovar, G. E. M., & Borchers, K. (2012). Stiff gelatin hydrogels can be photochemically synthesized from low viscous gelatin solutions using molecularly functionalized gelatin with a high degree of methacrylation. *Journal of Materials Science: Materials in Medicine,* 23(11), 2607-2617.
22. Teoh, B. T., Sam, S. S., Tan, K. K., Danlami, M. B., Shu, M. H., Johari, J., Abu Bakar, S. (2015). Early detection of dengue virus by use of reverse transcription recombinase polymerase amplification. *Journal of Clinical Microbiology,* 53(3), 830-837.
23. Gaines, M. L., Wojtkiewicz, P. W., Valentine, J. A., & Brown, C. L. (2002). Reduced Volume PCR Amplification Reactions Using the AmpF1STR® Profiler Plus™ Kit, *Journal of Forensic Sciences,* 47(6), 15554J.
24. Gurukumar, K., Priyadarshini, D., Patil, J., Bhagat, A., Singh, A., Shah, P., & Cecilia, D. (2009). Development of real time PCR for detection and quantitation of Dengue Viruses. *Virology Journal,* 6(1), 10.
25. Wang, D. (2017). Evaluation and improvement of LAMP assays for detection of *Escherichia coli* serogroups O26, O45, O103, O111, O121, O145, and O157. *African Health Sciences,* 17(4), 1011-1021. https://doi.org/10.4314/ahs.v17i4.8.
26. Kopecek, J. and Yang, J. (2007), Hydrogels as smart biomaterials. Polym. Int., 56: 1078-1098.
27. Choi, W., Yeom, S. Y., Kim, J., Jung, S., Jung, S., Shim, T. S., Choi, N. (2018). Hydrogel micropost-based qPCR for multiplex detection of miRNAs associated with Alzheimer's Disease. *Biosensors and Bioelectronics,* 101, 235-244.
28. Beyer, A., Pollok, S., Rudloff, A., Cialla-May, D., Weber, K., & Popp, J. (2016). Fast-Track, One-Step *E. coli* Detection: A Miniaturized Hydrogel Array Permits Specific Direct PCR and DNA Hybridization while Amplification. *Macromolecular Bioscience,* 1325-1333.
29. Mitra, R. D., & Church, G. M. (1999). In situ localized amplification and contact replication of many individual DNA molecules. In *Nucleic Acids Research* (Vol. 27).
30. Mujawar, L. H., Kuerten, J. G. M., Siregar, D. P., Van Amerongen, A., & Norde, W. (2014). Influence of the relative humidity on the morphology of inkjet printed spots of IgG on a non-porous substrate. *RSC Advances,* 4(37), 19380-19388.
31. Jung, S., Kim, B. K., Lee, S., Yoon, S., Im, H. I., & Kim, S. K. (2018). Multiplexed on chip real-time PCR using hydrogel spot array for microRNA profiling of minimal tissue samples. *Sensors and Actuators, B: Chemical,* 262, 118-124.
32. Thekisoe, 0. M. M., Bazie, R. S. B., Coronel-Servian, A. M., Sugimoto, C., Kawazu, S. I., & Inoue, N. (2009). Stability of Loop-Mediated Isothermal Amplification (LAMP) Reagents and its Amplification Efficiency on Crude Trypanosome DNA Templates. In *J. Vet. Med. Sci* (Vol. 71).
33. Dahl, A., Sultan, M., Jung, A., Schwartz, R., Lange, M., Steinwand, M., Nyarsik, L. (2007). Quantitative PCR based expression analysis on a nanoliter scale using polymer nano-well chips. *Biomedical Microdevices,* 9(3), 307-314

All references and publication cited in the specification and Examples are incorporated by reference herein in their entireties.

We claim:

1. A biogel nanosensor for detecting an analyte in a sample comprising:
   an acryloyl or a methacryloyl modified hydrogel on the surface of a substrate; and
   nucleic acid amplification reagents;
   wherein the hydrogel is crosslinked in picoliter or nanoliter volume on the surface of the substrate in a microarray form of spots, and the nucleic acid amplification reagents are layered in picoliter or nanoliter volume on the crosslinked hydrogel spots.

2. The biogel nanosensor of claim 1, wherein the total volume of hydrogel and nucleic acid amplification reagents in a spot of the microarray is in the range of about 0.1 nL to about 10 nL.

3. The biogel nanosensor of claim 1, wherein the hydrogel and nucleic acid amplification reagents are applied to the substrate by inkjet printing of picoliter drops for each spot of the microarray.

4. The biogel nanosensor of claim 1, wherein the modified hydrogel is a methacryloyl hydrogel, a methacryloyl acetylated hydrogel, a methacryloyl ethylene diamine, or combinations thereof.

5. The biogel nanosensor of claim 1, wherein the substrate is selected from the group consisting of glass, plastic, polymer, adhesive tape, paper, and titanium.

6. The biogel nanosensor of claim 1, wherein the substrate is a plastic selected from oriented polypropylene, polyethylene terephthalate, polyether sulfone, and polydimethylsiloxane.

7. The biogel nanosensor of claim 1, wherein the substrate surface is functionalized or coated with a polymer.

8. The biogel nanosensor of claim 1, further comprising a light guide.

9. The biogel nanosensor of claim 1, further comprising a heating element.

10. The biogel nanosensor of claim 9, wherein the heating element is in the biogel nanosensor or is connected to the biogel nanosensor externally.

11. The biogel nanosensor of claim 1, wherein the nucleic acid amplification reagents comprise DNA or RNA, at least one primer, at least one polymerase, and at least one detection element.

12. The biogel nanosensor of claim 11, wherein the detection element is fluorescent, colorimetric, or electrochemical.

13. A method of preparing a biogel nanosensor comprising:
   a) obtaining an acryloyl hydrogel or a methacryloyl hydrogel;
   b) printing the hydrogel in picoliter or nanoliter volume on the surface of a substrate in a microarray in the form of spots;
   c) crosslinking the hydrogel on the surface of the substrate; and
   d) combining nucleic acid amplification reagents in picoliter or nanoliter volume to the cross-linked hydrogel.

14. The method of claim 13, further comprising combining a light guide in the biogel nanosensor.

15. The method of claim 13, further comprising adding a heating element.

16. A method of detecting an analyte in a sample, comprising:
   contacting the biogel nanosensor of claim 1 with a sample containing at least one analyte; and
   measuring the presence of a detectable signal produced by at least one analyte in the sample.

17. The method of claim 16, wherein the biogel nanosensor further comprises a light guide.

18. The method of claim 16, wherein the sample contacts the crosslinked hydrogel and nucleic acid amplification reagent spots with a wicking matrix.

19. The method of claim 16, wherein measuring the presence of a detectable signal comprises applying a heating element to the biogel nanosensor after contact with the sample, and the heating element initiates nucleic acid amplification.

20. The method of claim 16, wherein the analyte is selected from a virus, bacteria, fungi, protozoa that contains ribonucleic acid, or a deoxyribonucleic acid or other polymer comprised of standard and nonstandard bases.

* * * * *